US011654298B2

(12) United States Patent
Baker et al.

(10) Patent No.: US 11,654,298 B2
(45) Date of Patent: May 23, 2023

(54) METHOD FOR TREATING CANCEROUS AND PRE-CANCEROUS SKIN

(71) Applicant: GenesisCare Ventures Pty Ltd, Alexandria (AU)

(72) Inventors: Christopher Baker, Alexandria (AU); Judith Mary Cole, Alexandria (AU); Robert Sinclair, Alexandria (AU); Warren Weightman, Alexandria (AU); Stephen Shumack, Alexandria (AU); Lynda Spelman, Alexandria (AU); Peter Foley, Alexandria (AU)

(73) Assignee: GenesisCare Ventures Pty Ltd, Alexandria (AU)

( * ) Notice: Subject to any disclaimer, the term of this patent is extended or adjusted under 35 U.S.C. 154(b) by 0 days.

(21) Appl. No.: 17/570,670

(22) Filed: Jan. 7, 2022

(65) Prior Publication Data
US 2022/0126115 A1 Apr. 28, 2022

Related U.S. Application Data

(63) Continuation of application No. 17/183,654, filed on Feb. 24, 2021, now Pat. No. 11,253,724.

(30) Foreign Application Priority Data

Jul. 1, 2020 (AU) .............................. 2020902243
Nov. 17, 2020 (AU) ..................... PCTAU202005242
Feb. 15, 2021 (AU) ................... PCTAU2021050129

(51) Int. Cl.
| *A61N 5/10* | (2006.01) |
| *A61K 35/00* | (2006.01) |
| *A61B 17/3205* | (2006.01) |
| *A61K 31/513* | (2006.01) |
| *A61K 31/4439* | (2006.01) |
| *A61N 5/06* | (2006.01) |
| *A61P 35/00* | (2006.01) |
| *A61P 17/02* | (2006.01) |
| *A61B 18/02* | (2006.01) |
| *A61B 17/00* | (2006.01) |
| *A61N 5/067* | (2006.01) |

(52) U.S. Cl.
CPC ............ *A61N 5/10* (2013.01); *A61B 17/3205* (2013.01); *A61K 31/4439* (2013.01); *A61K 31/513* (2013.01); *A61K 35/00* (2013.01); *A61N 5/062* (2013.01); *A61N 5/0616* (2013.01); *A61P 17/02* (2018.01); *A61P 35/00* (2018.01); *A61B 18/0218* (2013.01); *A61B 2017/00761* (2013.01); *A61N 5/067* (2021.08); *A61N 2005/0663* (2013.01)

(58) Field of Classification Search
CPC ........ A61N 5/10; A61N 5/062; A61N 5/0616; A61N 2005/0663; A61N 2005/067; A61K 31/513; A61K 35/00; A61K 31/4439; A61P 17/02; A61P 35/00; A61B 17/3205; A61B 18/0218; A61B 2017/00761
See application file for complete search history.

(56) References Cited

U.S. PATENT DOCUMENTS 11,253,724 B2 * 2/2022 Baker ..................... A61P 17/02

OTHER PUBLICATIONS

Chetty, P. et al., Primary Care Review of Actinic Keratosis and Its Therapeutic Options: A Global Perspective, Dermatology and Therapy(Heidelb), 5(1), Mar. 2015, pp. 19-35.
Dirschka, T. et al., A proposed scoring system for assessing the severity of actinic keratosis on the head: actinic keratosis area and severity index, Journal of the European Academy of Dermatology and Venereology, 31(8), Aug. 2017, pp. 1295-1302.
Dreno, B. et al., A Novel Actinic Keratosis Field Assessment Scale for Grading Actinic Keratosis Disease Severity, Acta Dermato-Venereologica, 97(9), Oct. 2017, pp. 1108-1113.
Emre, S. Actinic keratosis and field cancerization, World Journal of Dermatology, 5(2), May 2, 2016, pp. 115-124.
Esteva et al., "Dermatologist-level classification of skin cancer with deep neural networks," Nature, vol. 542, 12 pages (Jun. 29, 2017).
Nanni, L. et al., Deep learning for actinic keratosis classification, AIMS Electronics and Electrical Engineering, 4(1): Nov. 27, 2019, pp. 47-56.
Olsen et al., "A double-blind, vehicle-controlled study evaluation masoprocol cream in the treatment of actinic keratoses on the head and neck," Journal of the American Academy of Dermatology, vol. 23, No. 5, Part 1, pp. 738-743 (May 1991).
Schmitz, L. et al., Actinic keratosis area and severity index (AKASI) is associated with the incidence of squamous cell carcinoma, Journal of theEuropean Academy of Dermatology and Venereology, 32(5), May 2018, pp. 752-756.

* cited by examiner

*Primary Examiner* — Hasan S Ahmed
(74) *Attorney, Agent, or Firm* — McNeill Baur PLLC

(57) ABSTRACT

The present disclosure provides a method for treating clinical or pre-clinical skin damage in a skin field of a subject, wherein the skin field has been allocated a skin cancerization field index (SCR) score of at least 1 as determined by a process comprising the steps of: (i) assessing the number of keratoses in the skin field; (ii) assessing the thickness of the thickest keratosis in the skin field; and (iii) assessing the proportion of the field affected by clinical or subclinical skin damage. Based on the assessments made in (i), (ii) and (iii) the subject is optionally treated by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy.

16 Claims, No Drawings

METHOD FOR TREATING CANCEROUS AND PRE-CANCEROUS SKIN

SUMMARY AND BACKGROUND OF DISCLOSURE

The present application is a continuation of U.S. application Ser. No. 17/183,654, filed Feb. 24, 2021, which claims the benefit of PCT/AU2021/050129 filed on Feb. 15, 2021, which claims the benefit of PCT/AU2020/051242 filed on Nov. 17, 2020, which claims the benefit of Australian Provisional Application No. AU2020902243 filed Jul. 1, 2020, each of which is incorporated herein by reference in its entirety.

The present disclosure relates to methods of assessment, diagnosis, collecting data, and/or treatment of clinical and/or subclinical skin damage including cancerous and pre-cancerous skin. The method can be for one or more skin lesions and/or one or more skin fields. The disclosure particularly relates to improved methods of assessing the severity of skin abnormality and/or damage in a skin field, and optionally also the use of the assessment in the diagnosis and/or treatment of clinical and/or subclinical skin damage. The disclosure also relates to the use of the assessment to assess the efficacy of treatment.

Skin cancer is the out-of-control growth of abnormal cells in the epidermis, the outermost skin layer, caused by unrepaired DNA damage that triggers mutations. These mutations lead the skin cells to multiply rapidly and form malignant tumors. The main types of skin cancer are basal cell carcinoma (BCC), squamous cell carcinoma (SCC), melanoma, and Merkel cell carcinoma (MCC).

Skin field cancerization refers to the process in which a region or field of skin exhibits regional clinical and/or subclinical damage such as multiple lesions. This damage ranges from single UV-damaged keratinocytes, subclinical lesions, early clinical lesions, such as actinic keratosis and Bowen's disease, and advanced clinical lesions, invasive SCC and BCC. Some treatments for cancerous and pre-cancerous skin are directed to individual lesions and other treatments are skin field-directed.

Actinic keratosis (AK), the most common carcinoma in-situ of the skin, is a clinical manifestation of cutaneous 'field cancerization'. The understanding of actinic keratosis has evolved over time. It was previously considered a 'pre-malignant' lesion, but now understood to be carcinoma in-situ, with identical histological features to SCC, that may progress to invasive squamous cell carcinoma. Rates of progress of actinic keratosis to SCC has been reported as 0.025-16% per lesion, per year (Glogau 2000). Actinic keratoses are a common manifestation of skin field cancerization, with prevalence estimates ranging between 40-60% in adults over 40 years in Australia.

While the risk of transformation to invasive SCC of individual actinic keratoses is low, many patients have multiple actinic keratoses and multiple areas of skin affected by field cancerization, thus increasing their cumulative risk of malignant transformation. It has long been understood that given the inability to predict how an individual lesion will behave, all actinic keratoses should be treated.

Clinical and pre-clinical skin damage including actinic keratoses and the various skin cancers are notoriously variable. Diagnosis is difficult and assessing the severity of the condition even more challenging. Various tools have been developed over time to assist those skilled in the art to consistently and reproducibly assess the severity of skin lesions.

Until recently, these tools have been limited to clinical assessment tools designed to assess individual actinic keratoses, e.g. the Olsen tool (Olsen 1991), with no assessment of the surrounding skin field. Attempts to overcome this limitation by combining the Olsen tool with "lesion counts" have been plagued by poor inter-rater reliability, even among experts.

There is a need for improved tools for assessing skin field cancerization. It would be an advantage for the tool to have improved consistency and/or reproducibility.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE DISCLOSURE

The present disclosure provides a novel tool for assessing the severity of skin damage in a skin field. This optionally involves assessing preclinical and/or clinical skin damage. This optionally involves assessing skin field cancerization. The assessment of the severity is optionally associated with a severity score. The assessment and/or severity score is optionally useful in determining treatment selection.

In one aspect, the present disclosure provides a method for assessing the severity of clinical or pre-clinical skin damage in at least one skin field in a subject comprising
(i) assessing the number of keratoses in the skin field;
(ii) assessing the thickness of the thickest keratosis in the skin field;
(iii) assessing the proportion of the field affected by clinical or subclinical skin damage; and
assigning the skin field with a severity score based on the assessments made in (i), (ii) and (iii). In an alternative aspect, the present disclosure provides a method for assessing the severity of clinical or pre-clinical skin damage in at least one skin field in a subject comprising (i) assessing the number of keratoses in the skin field; (ii) assessing the thickness of the thickest keratosis in the skin field; (iii) assessing the proportion of the field affected by clinical or subclinical skin damage; and assigning the skin field with a severity score based on the assessments made in (i), (ii) and (iii), wherein the assessment of (i), (ii) and (iii) is performed on an image of the skin field. In a further alternative aspect, the present disclosure provides a method for assessing the severity of clinical or pre-clinical skin damage in at least one skin field in a subject comprising (a) obtaining one or more image of a skin field; and (b) (i) assessing the number of keratoses in the skin field; (ii) assessing the thickness of the thickest keratosis in the skin field; (iii) assessing the proportion of the field affected by clinical or subclinical skin damage; and assigning the skin field with a severity score based on the assessments made in (i), (ii) and (iii), wherein the assessment of (i), (ii) and (iii) is performed on the image of the skin field.

In another aspect, the present disclosure provides a method for assessing the severity of clinical or pre-clinical skin damage in at least one skin field in a subject comprising
(i) assessing the number of keratoses in the skin field and assigning the skin field with a score based on the result of the assessment;
(ii) assessing the thickness of the thickest keratosis in the skin field and assigning the skin field with a score based on the result of the assessment;

(iii) assessing the proportion of the field affected by clinical or subclinical skin damage and assigning the skin field with a score based on the result of the assessment; and assigning the skin field with a severity score based on the scores assigned in (i), (ii) and (iii). In an alternative aspect, the present disclosure provides a method for assessing the severity of clinical or pre-clinical skin damage in at least one skin field in a subject comprising (i) assessing the number of keratoses in the skin field and assigning the skin field with a score based on the result of the assessment; (ii) assessing the thickness of the thickest keratosis in the skin field and assigning the skin field with a score based on the result of the assessment; (iii) assessing the proportion of the field affected by clinical or subclinical skin damage and assigning the skin field with a score based on the result of the assessment; and assigning the skin field with a severity score based on the scores assigned in (i), (ii) and (iii) wherein the assessment of (i), (ii) and (iii) is performed on an image of the skin field. In a further alternative aspect, the present disclosure provides a method for assessing the severity of clinical or pre-clinical skin damage in at least one skin field in a subject comprising (a) obtaining one or more image of a skin field; and (b) (i) assessing the number of keratoses in the skin field and assigning the skin field with a score based on the result of the assessment; (ii) assessing the thickness of the thickest keratosis in the skin field and assigning the skin field with a score based on the result of the assessment; (iii) assessing the proportion of the field affected by clinical or subclinical skin damage and assigning the skin field with a score based on the result of the assessment; and assigning the skin field with a severity score based on the scores assigned in (i), (ii) and (iii) wherein the assessment of (i), (ii) and (iii) is performed on the image of the skin field.

In a further aspect, the present disclosure provides a method for classifying a subject for eligibility for skin field therapy comprising (i) assessing the number of keratoses in the skin field and assigning the skin field with a score based on the result of the assessment;

(ii) assessing the thickness of the thickest keratosis in the skin field and assigning the skin field with a score based on the result of the assessment;

(iii) assessing the proportion of the field affected by clinical or subclinical skin damage and assigning the skin field with a score based on the result of the assessment; and assigning the skin field with a severity score based on the scores assigned in (i), (ii) and (iii). In an alternative aspect, the present disclosure provides a method for classifying a subject for eligibility for skin field therapy comprising (i) assessing the number of keratoses in the skin field and assigning the skin field with a score based on the result of the assessment; (ii) assessing the thickness of the thickest keratosis in the skin field and assigning the skin field with a score based on the result of the assessment; (iii) assessing the proportion of the field affected by clinical or subclinical skin damage and assigning the skin field with a score based on the result of the assessment; and assigning the skin field with a severity score based on the scores assigned in (i), (ii) and (iii) wherein the assessment of (i), (ii) and (iii) is performed on an image of the skin field. In a further alternative aspect, the present disclosure provides a method for classifying a subject for eligibility for skin field therapy comprising (a) obtaining one or more image of a skin field; and (b) (i) assessing the number of keratoses in the skin field and assigning the skin field with a score based on the result of the assessment; (ii) assessing the thickness of the thickest keratosis in the skin field and assigning the skin field with a score based on the result of the assessment; (iii) assessing the proportion of the field affected by clinical or subclinical skin damage and assigning the skin field with a score based on the result of the assessment; and assigning the skin field with a severity score based on the scores assigned in (i), (ii) and (iii) wherein the assessment of (i), (ii) and (iii) is performed on the image of the skin field.

The present disclosure further provides a non-invasive method for collecting data useful for determining severity of clinical or pre-clinical skin damage at least one skin field in a subject, the method comprising:

(i) assessing the number of keratoses in the skin field and assigning the skin field with a score based on the result of the assessment;

(ii) assessing the thickness of the thickest keratosis in the skin field and assigning the skin field with a score based on the result of the assessment; and (iii) assessing the proportion of the field affected by clinical or subclinical skin damage and assigning the skin field with a score based on the result of the assessment. Alternatively, the present disclosure further provides, a non-invasive method for collecting data useful for determining severity of clinical or pre-clinical skin damage at least one skin field in a subject, the method comprising (i) assessing the number of keratoses in the skin field and assigning the skin field with a score based on the result of the assessment; (ii) assessing the thickness of the thickest keratosis in the skin field and assigning the skin field with a score based on the result of the assessment; and (iii) assessing the proportion of the field affected by clinical or subclinical skin damage and assigning the skin field with a score based on the result of the assessment, wherein the assessment of (i), (ii) and (iii) is performed on an image of the skin field. Alternatively, the present disclosure further provides, a non-invasive method for collecting data useful for determining severity of clinical or pre-clinical skin damage at least one skin field in a subject, the method comprising (a) obtaining one or more image of a skin field; and (b) (i) assessing the number of keratoses in the skin field and assigning the skin field with a score based on the result of the assessment; (ii) assessing the thickness of the thickest keratosis in the skin field and assigning the skin field with a score based on the result of the assessment; and (iii) assessing the proportion of the field affected by clinical or subclinical skin damage and assigning the skin field with a score based on the result of the assessment, wherein the assessment of (i), (ii) and (iii) is performed on the image of the skin field.

The present disclosure also provides a non-invasive method for collecting data useful for classifying a subject for eligibility for skin field therapy, the method comprising:

(i) assessing the number of keratoses in the skin field and assigning the skin field with a score based on the result of the assessment;

(ii) assessing the thickness of the thickest keratosis in the skin field and assigning the skin field with a score based on the result of the assessment; and (iii) assessing the proportion of the field affected by clinical or subclinical skin damage and assigning the skin field with a score based on the result of the assessment. Alternatively, the present disclosure further provides, a non-invasive method for collecting data useful for classifying a subject for eligibility for skin field therapy, the method comprising (i) assessing the number of keratoses in the skin field and assigning the skin field with a score based on the result of the assessment; (ii) assessing the thickness of the thickest keratosis in the skin field and assigning the skin field with a score based on the result of the assessment; and (iii) assessing the proportion of the field affected by clinical or subclinical skin damage and assigning the skin field with a score based on the result of the assessment, wherein the assessment of (i), (ii) and (iii) is performed on an image of the skin field. Alternatively, the present disclosure further provides, a non-invasive method for collecting data useful for classifying a subject for eligibility for skin field therapy, the method comprising (a) obtaining one or more image of a skin field; and (b) (i) assessing the number of keratoses in the skin field and assigning the skin field with a score based on the result of the assessment; (ii) assessing the thickness of the thickest keratosis in the skin field and assigning the skin field with a score based on the result of the assessment; and (iii) assessing the proportion of the field affected by clinical or subclinical skin damage and assigning the skin field with a score based on the result of the assessment, wherein the assessment of (i), (ii) and (iii) is performed on the image of the skin field.

The present disclosure also provides a method for treating clinical or pre-clinical skin damage in a subject in need thereof comprising selecting at least one skin field
  (i) assessing the number of keratoses in the skin field;
  (ii) assessing the thickness of the thickest keratosis in the skin field;
  (iii) assessing the proportion of the field affected by clinical or subclinical skin damage; and
based on the assessments made in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy.

The present disclosure also provides a method of treating clinical or pre-clinical skin damage in a subject in need thereof comprising selecting at least one skin field
  (i) assessing the number of keratoses in the skin field and assigning the skin field with a score based on the result of the assessment;
  (ii) assessing the thickness of the thickest keratosis in the skin field and assigning the skin field with a score based on the result of the assessment;
  (iii) assessing the proportion of the field affected by clinical or subclinical skin damage and assigning the skin field with a score based on the result of the assessment; and
based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy.

In a further aspect, the present disclosure provides a method for monitoring the response of a subject to treatment for clinical or pre-clinical skin damage, the method comprising
  (i) assessing the number of keratoses in the skin field and assigning the skin field with a score based on the result of the assessment;
  (ii) assessing the thickness of the thickest keratosis in the skin field and assigning the skin field with a score based on the result of the assessment;
  (iii) assessing the proportion of the field affected by clinical or subclinical skin damage and assigning the skin field with a score based on the result of the assessment; and
based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy, and
following treatment repeating assessments (i), (ii) and (iii) and comparing the initial and repeated assessments to monitor the subject's response to the treatment. Optionally, the assessment of (i), (ii) and (iii) is performed on an image of the skin field.

Alternatively, the present application provides a method for monitoring the response of a subject to treatment for clinical or pre-clinical skin damage, the method comprising
  a) prior to the subject receiving treatment
    (i) assessing the number of keratoses in the skin field and assigning the skin field with a score based on the result of the assessment;
    (ii) assessing the thickness of the thickest keratosis in the skin field and assigning the skin field with a score based on the result of the assessment;
    (iii) assessing the proportion of the field affected by clinical or subclinical skin damage and assigning the skin field with a score based on the result of the assessment; and
  b) after the subject receiving treatment, repeating assessments (i), (ii) and (iii);
  and comparing the assessments of a) and b) to monitor the subject's response to the treatment. Optionally, a decrease in any one or more of the scores for (i), (ii) and (iii) obtained in b) as compared to any one or more of the scores of i), (ii) and (iii) obtained in a) is indicative of the subject responding to the treatment, and/or is indicative of improvement resulting from the treatment in the clinical and/or pre-clinical skin damage. Optionally, the assessment of (i), (ii) and (iii) is performed on an image of the skin field.

In a further alternate aspect, the present application provides a method for monitoring the response of a subject to treatment for clinical or pre-clinical skin damage, the method comprising
  a) prior to the subject receiving treatment, obtaining one or more image of the skin field and
    (i) assessing the number of keratoses in the skin field and assigning the skin field with a score based on the result of the assessment;
    (ii) assessing the thickness of the thickest keratosis in the skin field and assigning the skin field with a score based on the result of the assessment;
    (iii) assessing the proportion of the field affected by clinical or subclinical skin damage and assigning the skin field with a score based on the result of the assessment; and
  b) after the subject receiving treatment, obtaining one or more image of the skin field, and repeating assessments (i), (ii) and (iii);
  and comparing the assessments of a) and b) to monitor the subject's response to the treatment,
wherein the assessments of (i), (ii) and (iii) are performed on an image of the skin field.

Optionally, a decrease in any one or more of the scores for (i), (ii) and (iii) obtained in b) as compared to any one or more of the scores of i), (ii) and (iii) obtained in a) is indicative of the subject responding to the treatment, and/or is indicative of improvement resulting from the treatment in the clinical and/or pre-clinical skin damage.

In the aspects of disclosure that do not already include calculation of a severity score, optionally, a severity score is assigned to the skin field based on the scores assigned in (i), (ii) and (iii). In these embodiments or the aspects of the disclosure requiring a severity score, optionally the severity score cannot be zero. Optionally, the score assigned in assessment (i) is at least 1. Optionally, the severity score is an SCFI as described elsewhere in the specification.

In embodiments involving comparing scores before and after treatment, optionally, a decrease in the severity score based on the scores of (i), (ii) and (iii) obtained in b) as compared to the severity score based on the scores of i), (ii) and (iii) obtained in a) is indicative of the subject responding to the treatment, and/or is indicative of improvement resulting from the treatment in the clinical and/or pre-clinical skin damage. Optionally, the severity score is an SCFI as described elsewhere in the specification.

In some embodiments, assessment (i) involves assessing the skin field as including no, mild, moderate, or severe keratoses. Specifically, this assessment involves categorization of the skin field into one of four categories consisting of no, mild, moderate, and severe keratoses. Mild actinic keratosis is understood by a person skilled in the art to refer to one or more discrete lesions. Optionally, there are 5 or fewer discrete lesions, preferably 1 to 5 lesions. Moderate actinic keratosis is understood by a person skilled in the art to refer to greater numbers of discrete lesions. Moderate actinic keratosis refers to more than 5 lesions where there are no continuous keratoses. Optionally, there are 15 or fewer lesions, preferably 6 to 15 lesions. Severe actinic keratosis is understood by a person skilled in the art to refer to either continuous actinic keratoses, large lesions numbers or a combination of both. Keratoses are continuous if the individual lesions are no longer individually distinct (ie they run into each other). Optionally, there are continuous keratoses and/or more than 15 lesions.

An assessment of the severity of skin lesions can be difficult when based on lesion counts, particularly at high lesion numbers. Methods that focus on the nature of the lesions were found, during development of the disclosure, to be less precise than counting at lower lesion numbers and could result in redundancy with affected area scores. This disclosure uses a combination of counting discrete lesions (only requiring a count up to 15) and assessment of when the nature of the lesions turns from discrete to continuous. This combination is thought to result in good repeatability and inter-rater agreement of the assessment for both mild and severe skin damage.

In some embodiments, a score of 0-3 is allocated for the skin field assessed in assessment (i) for no, mild, moderate, or severe keratoses, respectively. Specifically, no keratosis receives a score of 0, mild keratosis a score of 1, moderate keratosis a score of 2, and severe keratosis a score of 3.

In alternative embodiments, a score of 0-3 is allocated for the skin field assessed in assessment (i) as follows:
  0 for no discrete or continuous lesions;
  1 for 5 or fewer (for example 1 to 5) discrete lesions in the skin field and no continuous keratosis;
  2 for more than 5 discrete lesions in the skin field and no continuous keratoses; and
  3 for continuous keratosis and/or more than 15 discrete lesions in the skin field.

Optionally, the score of 2 is further allocated because there are 15 or fewer lesions (for example, 6 to 15 lesions) in the skin field.

In some embodiments, assessment (ii) in the above aspects of disclosure comprises assessment in accordance with the Olsen score, a modified Olsen score, direct measurement of the thickness of the keratosis and/or indirect measurement of thickness of the actinic keratosis by measurement of the stratum corneum hydration of the actinic keratosis. Optionally, a score of 0-3 is allocated for the skin field assessed in assessment (ii) for <1 mm thick, about 1 mm thick, >1-3 mm thick and >3 mm thick respectively.

In some embodiments, assessment (ii) involves assessing the thickest keratoses in the skin field as having no thickness, having thin or just perceptible thickness (eg about 1 mm), having moderate or easily felt or seen thickness (eg >1 to about 3 mm), or being very thick including having cutaneous horns (eg >3 mm). This is a modified Olsen score. Further detail on the Olsen score is provided in the detailed description. Optionally, a score of 0-3 is allocated for the skin field assessed in assessment (ii) for no thickness, thin thickness, moderate thickness or very thick, respectively. Specifically, no thickness receives a score of 0, thin thickness a score of 1, moderate thickness a score of 2, and very thick a score of 3.

Optionally, assessment (ii) involves touching the skin. Alternatively, assessment (ii) does not involve touching the skin. For example, the assessment occurs by way of photographic or video review.

In some embodiments, assessment (iii) involves assessing whether no area, 1-5% of the area, less than ⅓ of the area, ⅓-⅔ of the area, greater than ⅔ of the area to 95% of the area, or 96-100% of the area in the skin field is affected by clinical or pre-clinical skin damage. Optionally, a score of 0-5 is allocated for the skin field assessed in assessment (iii) for no area of affected, 1-5% of the area affected, less than ⅓ of the area affected, ⅓-⅔ of the area affected, greater than ⅔ of the area to 95% of the area affected, or 96-100% of the area affected, respectively.

In alternative embodiments, assessment (iii) involves assessing whether no area, 1-5% of the area, 6-33% of the area, 34-66% of the area, 67-95% of the area, or 96-100% of the area in the skin field is affected by clinical or pre-clinical skin damage. Optionally, a score of 0-5 is allocated for the skin field assessed in assessment (iii) for no area of affected, 1-5% of the area, 6-33% of the area, 34-66% of the area, 67-95% of the area, or 96-100% of the area, respectively.

In at least one aspect of the present disclosure, the skin cancerization field index (SCFI) score is determined for the skin field. The SCFI score is determined by adding the score for assessment (i) as described above to the score for assessment (ii) as described above and then multiplying the sum of those scores by the score for assessment (iii) as described above. The SCFI can be from 0 to 30 in total.

The present disclosure is also intended to cover scores of equivalent weighting to those specifically recited herein. Scores of equivalent weighting include scores from any scoring system where the scores have been scaled up or down from the 0 to 30 SCFI score but can still be correlated to the appropriate treatment based on work done by the assessors. For example, instead of a score of 0 to 3 for assessment (i), 0 to 3 for assessment (ii), and 0 to 5 for assessment (iii) resulting in a SCFI of 0 to 30, the score could be 0 to 6 for assessment (i), 0 to 6 for assessment (ii), and 0 to 10 for assessment (iii) resulting in a SCFI of 0 to 120, or the score could be 0 to 1.5 for assessment (i), 0 to 1.5 for assessment (ii), and 0 to 2.5 for assessment (iii) resulting in a SCFI of 0 to 7.5. In this instance, the correlation between the score and the appropriate treatment can be scaled by the skilled person for other scores of equivalent weight to the scores provided above. In addition to increasing or decreasing the score scale by a factor of 2, a score of equivalent weighting includes a score where the results are increased or decreased by a factor of 3, 4, 5, 6, 7, 8, 9, or 10 or any other change in scale that retains the relationships between the results as determined and described in the present disclosure. Thus, throughout the disclosure, the scores recited herein should be considered to include scores of equivalent weighting such as those arrived at by altering the scale.

Assessments (i), (ii) and/or (iii) are optionally determined from one or more physical or electronic photographs, video, scans or non-invasive imaging techniques (including for example high definition OCT (optical coherence tomography), RCM (reflectance confocal microscopy) or HFUS (high frequency ultrasound) typically in the 20 MHz range. The images can be physical, such as printed, or electronic. Optionally, there are multiple still images such as photographs from different angles, or stereo imaging systems. However, a single photograph has been shown to be effective so long as it is close enough and of sufficient quality to properly visualize the skin damage. A suitable image is optionally isolated from a video. The video can be recorded or streamed to the assessor.

Assessments (i), (ii) and/or (iii) may be made by a medical professional such as a general practitioner, dermatologist, oncologist, radiologist or nurse. Optionally, the nurse is a dermatology, oncology or radiology nurse. Alternatively, the assessments may be made using artificial intelligence (AI) including computer vision systems to process and evaluate images of the skin.

The assessment of the subject's skin including assessments (i), (ii) and (iii) may involve visual assessment or dermoscopic analysis, analysis of one or more images of the subject's skin using one or more of the above imaging techniques, reference to one or more biopsy (histopathology) results for one or more of the subject's lesions, and/or reference to the subject's medical history (such as a prior skin cancer diagnosis). In some embodiments, assessment is performed by a computer program. For example, the visual assessment; photographic, RCM, OCT or HFUS analysis; reference to biopsy results; reference to histopathology results; and/or reference to the subject's medical history is optionally conducted by one or more computer programs. Programs using artificial intelligence (AI) to assess the severity of actinic keratosis have been developed and are expected to be adaptable to conduct the assessment of this disclosure and inform the user regarding the severity of a skin field and/or the suitable treatment.

In particular, various types of classifiers including Bayesian, ensemble or SVM (support vector machine) classifiers may be used in conjunction with training data in the form of images generated for assessments (i), (ii) and/or (iii) as well as other selected images of healthy and affected skin. The classifiers may also be trained using results from the manual skin scoring method of the disclosure.

In some embodiments, the skin field is further assessed for the presence of cancer in the skin field and/or a histologically proven history of cancer in the skin field within the past 6 months.

In some embodiments, the method does not involve the assessment of the subject's erythema.

In some embodiments, two or more skin fields are assessed on one subject. Optionally, two or more skin fields are assessed on one subject and a separate score allocated for each field.

In some embodiments, the subject has an SCFI score of 15 or more (ie 15-30) and is treated with a skin field therapy. More specifically, the skin field therapy is recommended at least in part because the SCFI is 15 or more. In accordance with the rest of the specification, these statements also apply to scores of equivalent weighting.

Optionally, the treatment of the subject's clinical or preclinical skin damage prevents the development of skin cancer or further skin cancers. Alternatively, or additionally, the treatment reduces the clinical and/or pre-clinical skin damage in the skin field.

Optionally, the skin field therapy is radiation therapy or the field application of a topical treatment. Suitable topical treatments include application of topical 5-fluorouracil, imiquimod, ingenol mebutate, diclofenac or photodynamic therapy. The radiation therapy or topical treatment is applied to at least the affected area in the field. In some embodiments, the radiation therapy includes one or more lesional tumorcidal radiation therapy boosts to treat one or more specific lesions, such as lesions of greater than 5 mm in diameter, or one or more non-melanoma skin cancers, such as SCCs or BCCs.

In some embodiments, the subject has (a) an SCFI score of 15 or more, and (b) the skin field includes 1 or more cancerous lesions. There are simultaneous cancerous lesions when there are two or more cancerous lesions occurring in the skin field at the same time. In those embodiments, the subject is optionally treated with (i) radiation therapy including one or more lesional tumorcidal radiation therapy boosts to treat the cancerous lesions, or (ii) surgical removal of the cancerous lesions followed by field radiation therapy.

In some embodiments, the skin field has an SCFI score of 1-14 and is treated with a lesional therapy. Optionally, the lesional therapy is (a) freezing one or more lesions with liquid nitrogen, (b) shaving, curetting or surgically removing one or more lesions, or (c) applying a topical treatment to one or more lesions. Optionally, the topical treatment is 5-fluorouracil, imiquimod, ingenol mebutate, diclofenac or photodynamic therapy. The topical treatment is applied to one or more lesions. In accordance with the rest of the specification, these statements also apply to scores of equivalent weighting.

In some embodiments, the skin field has an SCFI score of 1-14 and the skin field includes 3 or more simultaneous cancerous lesions. In these embodiments, the patient is optionally treated with a field therapy. Optionally, the skin field is treated with radiation therapy including one or more lesional tumorcidal radiation therapy boosts to treat the cancerous lesions, or surgical removal of the cancerous lesions followed by field radiation therapy. In accordance with the rest of the specification, these statements also apply to scores of equivalent weighting.

In some embodiments, the skin field is further assessed for the presence of cancer in the skin field and/or a histologically proven history of cancer in the skin field within the past 6 months. Optionally, where the SCFI score for the skin field is 1-14 (preferably 10-14) and the skin field is assessed as (i) including skin cancer, or (ii) having a histologically proven history of cancer, then the treatment provided to the subject is a skin field treatment. Optionally, the patient is treated with radiation therapy including one or more lesional tumorcidal radiation therapy boosts to treat the cancerous lesions, or surgical removal of the cancerous lesions followed by field radiation therapy. In accordance with the rest of the specification, these statements also apply to scores of equivalent weighting.

In some embodiments, the subject has an SCFI score of 10 or greater and is treated with a skin field therapy. In some embodiments, when the subject has an SCFI score of 10 or greater, the subject is treated with a skin field therapy and, when the subject has an SCFI score of 1 to 9, the subject is treated with a lesional therapy. Optionally, the skin field therapy is radiation therapy or the field application of a topical treatment.

In some embodiments, the skin field has an SCFI score of 10 or greater and is treated with a skin field therapy. In some embodiments, when the skin field has an SCFI score of 10 or greater, the skin field is treated with a skin field therapy and, when the skin field has an SCFI score of 1 to 9, the skin field is treated with a lesional therapy. Optionally, the skin field therapy is radiation therapy or the field application of a topical treatment.

In some embodiments, the skin field has an SCFI of 10 to 19 and is treated with the field application of a topical treatment. In other embodiments, the skin field has an SCFI of 20 to 30 and is treated with either field radiation therapy or the field application of a topical treatment. Optionally, (i) when the skin field has an SCFI score of 20 to 30, the skin field is treated with field radiotherapy or the field application of a topical treatment; (ii) when the skin field has an SCFI of 10 to 19, the skin field is treated with the field application of a topical treatment; and (iii) when the skin field has an SCFI score of 1 to 9, the skin field is treated with a lesional therapy.

In some embodiments, the skin field has an SCFI of 20 to 25 and is treated with either field radiation therapy or the field application of a topical treatment. In other embodiments, the skin field has an SCFI of 26 to 30 and is treated with field radiation therapy. Optionally, (i) when the skin field has an SCFI score of 26 to 30, the skin field is treated with field radiotherapy; (ii) when the skin field has an SCFI score of 20 to 25, the skin field is treated with field radiotherapy or the field application of a topical treatment; (iii) when the skin field has an SCFI of 10 to 19, the skin field is treated with the field application of a topical treatment; and (iv) when the skin field has an SCFI score of 1 to 9, the skin field is treated with a lesional therapy.

In some embodiments, the skin field has an SCFI of 24 or 25 and a 3 for the score of assessment (ii) and is treated with field radiation therapy. Optionally, (i) when the skin field has an SCFI score of 26 to 30, the skin field is treated with field radiotherapy; (ii) when the skin field has an SCFI score of 24 or 25 and a 3 for the score of assessment (ii), the skin field is treated with field radiotherapy; (iii) when the skin field has an SCFI score of 20 to 25 but not a score of 24 or 25 with a 3 for the score of assessment (ii), the skin field is treated with field radiotherapy or the field application of a topical treatment; (iv) when the skin field has an SCFI of 10 to 19, the skin field is treated with the field application of a topical treatment; and (v) when the skin field has an SCFI score of 1 to 9, the skin field is treated with a lesional therapy.

In some embodiments, where a field topical treatment is applied and the topical treatment does not adequately treat the skin field, the skin field is subsequently treated with field radiation therapy.

The present disclosure also provides a method for treating clinical or pre-clinical skin damage in a skin field of a subject, wherein the skin field has been allocated a skin cancerization field index (SCFI) score of at least 1 as determined by a process comprising the steps of:
  (a) selecting and assessing at least one skin field for
    (i) the number of keratoses in the skin field;
    (ii) the thickness of the thickest keratosis in the skin field; and
    (iii) the proportion of the field affected by clinical or subclinical skin damage;
  (b) assigning a score of 0 to 3 for assessment (i), a score of 0 to 3 for assessment (ii), and a score of 0 to 5 for assessment (iii); and
  (c) adding the score for assessment (i) to the score for assessment (ii) and then multiplying the sum of those scores by the score for assessment (iii) to obtain the SCFI score;
the method for treating comprising:
  A. treating the skin field with a field therapy when the SCFI score is 10 or greater; or
  B. treating the skin field with a lesional therapy when the SCFI score is 1 to 9.

In accordance with the rest of the specification, these statements also apply to scores of equivalent weighting.

The present disclosure also provides a method for administering radiation therapy in a skin field of a subject, wherein the skin field has been allocated a skin cancerization field index (SCFI) score of at least 20 as determined by a process comprising the steps of:
  (a) selecting and assessing at least one skin field for
    (i) the number of keratoses in the skin field;
    (ii) the thickness of the thickest keratosis in the skin field; and
    (iii) the proportion of the field affected by clinical or subclinical skin damage;
  (b) assigning a score of 0 to 3 for assessment (i), a score of 0 to 3 for assessment (ii), and a score of 0 to 5 for assessment (iii); and
  (c) adding the score for assessment (i) to the score for assessment (ii) and then multiplying the sum of those scores by the score for assessment (iii) to obtain the SCFI score;
the method for treating comprising administering radiation therapy to the skin field of the subject. Optionally, the skin field is confirmed to have an SCFI of 26 to 30 or of 24 or 25 and a 3 for the score of assessment (ii).

In accordance with the rest of the specification, these statements also apply to scores of equivalent weighting. The present disclosure also provides a method for administering topical therapy in a skin field of a subject, wherein the skin field has been allocated a skin cancerization field index (SCFI) score of at least 10 as determined by a process comprising the steps of:
  (a) selecting and assessing at least one skin field for
    (i) the number of keratoses in the skin field;
    (ii) the thickness of the thickest keratosis in the skin field; and
    (iii) the proportion of the field affected by clinical or subclinical skin damage;
  (b) assigning a score of 0 to 3 for assessment (i), a score of 0 to 3 for assessment (ii), and a score of 0 to 5 for assessment (iii); and
  (c) adding the score for assessment (i) to the score for assessment (ii) and then multiplying the sum of those scores by the score for assessment (iii) to obtain the SCFI score;
the method for treating comprising administering topical therapy to the skin field of the subject. Optionally, the SCFI of the skin field is 10 to 19. Optionally, the skin field is confirmed to have an SCFI of 10 to 25. Optionally, the skin field is confirmed to have an SCFI of 10 to 25 but not a score of 24 or 25 with a 3 for the score of assessment (ii). In accordance with the rest of the specification, these statements also apply to scores of equivalent weighting.

The present disclosure also provides a method for administering lesional therapy in a skin field of a subject, wherein the skin field has been allocated a skin cancerization field index (SCFI) score of 1-9 as determined by a process comprising the steps of:
 (a) selecting and assessing at least one skin field for
  (i) the number of keratoses in the skin field;
  (ii) the thickness of the thickest keratosis in the skin field; and
  (iii) the proportion of the field affected by clinical or subclinical skin damage;
 (b) assigning a score of 0 to 3 for assessment (i), a score of 0 to 3 for assessment (ii), and a score of 0 to 5 for assessment (iii); and
 (c) adding the score for assessment (i) to the score for assessment (ii) and then multiplying the sum of those scores by the score for assessment (iii) to obtain the SCFI score;
 the method for treating comprising administering topical therapy to the skin field of the subject. In accordance with the rest of the specification, these statements also apply to scores of equivalent weighting.

Alternatively, the present disclosure provides a method for treating clinical or pre-clinical skin damage in a skin field of a subject with a skin cancerization field index (SCFI) score of at least 1, the method comprising the steps of:
 determining a skin cancerization field index (SCFI) score by
 (a) selecting and assessing at least one skin field for
  (i) the number of keratoses in the skin field;
  (ii) the thickness of the thickest keratosis in the skin field; and
  (iii) the proportion of the field affected by clinical or subclinical skin damage; and
 (b) assigning a score of 0 to 3 for assessment (i), a score of 0 to 3 for assessment (ii), and a score of 0 to 5 for assessment (iii);
 (c) adding the score for assessment (i) to the score for assessment (ii) and then multiplying the sum of those scores by the score for assessment (iii) to obtain the SCFI score; and
 treating the clinical or pre-clinical skin damage, wherein
  if the SCFI score is 10 or greater, then the skin damage is treated with a field therapy; and
  if the SCFI score is 1 to 9, then the skin damage is treated with a lesional therapy.

In accordance with the rest of the specification, these statements also apply to scores of equivalent weighting.

The present disclosure also provides a method for treating clinical or pre-clinical skin damage in a subject as determined by a process comprising
 (a) selecting and assessing at least one skin field for
  (i) the number of keratoses in the skin field;
  (ii) the thickness of the thickest keratosis in the skin field;
  (iii) the proportion of the field affected by clinical or subclinical skin damage; and
 (b) assigning a score of 0 to 3 for (i), a score of 0 to 3 for (ii), and a score of 0 to 5 for (iii);
 (c) determining the skin cancerization field index (SCFI) score by adding the score for assessment (i) to the score for assessment (ii) and then multiplying the sum of those scores by the score for assessment (iii);
 the method comprising:
  A. treating the skin field with a field therapy when the SCFI score is 10 or greater; or
  B. treating the skin field with a lesional therapy when the SCFI score is 1 to 9.

In accordance with the rest of the specification, these statements also apply to scores of equivalent weighting.

Optionally, the skin field therapy is radiation therapy or the field application of a topical treatment. Optionally, the score must be greater than zero. Optionally, the SCFI score is at least 1. Optionally, when the skin field has an SCFI of 10 to 19, the skin field is treated with the field application of a topical treatment. Optionally, when the skin field has an SCFI of 20 to 30, the skin field is treated with either field radiation therapy or the field application of a topical treatment. Optionally, when the skin field has an SCFI of 20 to 25, the skin field is treated with either field radiation therapy or the field application of a topical treatment. Optionally, the skin field has an SCFI of 26 to 30 and is treated with field radiation therapy. Optionally, the skin field has an SCFI of 24 or 25 and a 3 for the score of assessment (ii) and is treated with field radiation therapy. In accordance with the rest of the specification, these statements also apply to scores of equivalent weighting.

The present disclosure also provides a method of administering skin field treatment to a subject comprising confirming that the subject is in need of a skin field treatment by:
 (a) selecting and assessing at least one skin field for
  (i) the number of keratoses in the skin field;
  (ii) the thickness of the thickest keratosis in the skin field;
  (iii) the proportion of the field affected by clinical or subclinical skin damage; and
 (b) assigning a score of 1 to 3 for (i), a score of 0 to 3 for (ii), and a score of 0 to 5 for (iii) (or scores of equivalent weighting);
 (c) determining the skin cancerization field index (SCFI) score by adding the score for assessment (i) to the score for assessment (ii) and then multiplying the sum of those scores by the score for assessment (iii);
 (d) confirming the SCFI is 10 or more;
 administering a skin field therapy to the skin field of the subject. Optionally, the skin field therapy is radiation therapy or field application of a topical therapy. Optionally, the skin field is confirmed to have an SCFI of 20 to 30. Optionally, when the skin field has an SCFI of 10 to 19, the skin field is treated with the field application of a topical treatment. Optionally, when the subject has an SCFI score of 26 to 30, the subject is treated with field radiotherapy. Optionally, when the subject has an SCFI score of 20 to 25, the subject is treated with field radiotherapy or the field application of a topical treatment. In accordance with the rest of the specification, these statements also apply to scores of equivalent weighting.

The present disclosure also provides a method of administering radiation treatment to a subject comprising confirming that the subject is in need of radiation treatment by:
 (a) selecting and assessing at least one skin field for
  (i) the number of keratoses in the skin field;
  (ii) the thickness of the thickest keratosis in the skin field;
  (iii) the proportion of the field affected by clinical or subclinical skin damage; and (b) assigning a score of 1 to 3 for (i), a score of 0 to 3 for (ii), and a score of 0 to 5 for (iii);

(c) determining the skin cancerization field index (SCFI) score by adding the score for assessment (i) to the score for assessment (ii) and then multiplying the sum of those scores by the score for assessment (iii);

(d) confirming the SCFI is 10 or more;

administering radiation therapy to the skin field of the subject. Optionally, the skin field is confirmed to have an SCFI of 20 to 30. Optionally, the skin field is confirmed to have an SCFI of 26 to 30. Optionally, the skin field is confirmed to have an SCFI score of 26 to 30 or of 24 or 25 and a 3 for the score of assessment (ii). In accordance with the rest of the specification, these statements also apply to scores of equivalent weighting.

The present disclosure also provides a method of administering a topical skin field treatment to a subject comprising confirming that the subject is in need of a topical skin field treatment by:

(a) selecting and assessing at least one skin field for
   (i) the number of keratoses in the skin field;
   (ii) the thickness of the thickest keratosis in the skin field;
   (iii) the proportion of the field affected by clinical or subclinical skin damage; and (b) assigning a score of 1 to 3 for (i), a score of 0 to 3 for (ii), and a score of 0 to 5 for (iii);

(c) determining the skin cancerization field index (SCFI) score by adding the score for assessment (i) to the score for assessment (ii) and then multiplying the sum of those scores by the score for assessment (iii);

(d) confirming the SCFI is 10 or more;

administering topical skin field therapy to the skin field of the subject. Optionally, when the skin field has an SCFI of 10 to 19, Optionally, the skin field is confirmed to have an SCFI of 20 to 30). Optionally, the skin field is confirmed to have an SCFI of 10 to 25. Optionally, the skin field is confirmed to have an SCFI of 10 to 25 but not a score of 24 or 25 with a 3 for the score of assessment (ii). In accordance with the rest of the specification, these statements also apply to scores of equivalent weighting.

The present disclosure also provides a method of administering a lesional skin field treatment to a subject comprising confirming that the subject is in need of a lesional skin field treatment by:

(a) selecting and assessing at least one skin field for
   (i) the number of keratoses in the skin field;
   (ii) the thickness of the thickest keratosis in the skin field;
   (iii) the proportion of the field affected by clinical or subclinical skin damage; and (b) assigning a score of 1 to 3 for (i), a score of 0 to 3 for (ii), and a score of 0 to 5 for (iii);

(c) determining the skin cancerization field index (SCFI) score by adding the score for assessment (i) to the score for assessment (ii) and then multiplying the sum of those scores by the score for assessment (iii);

(d) confirming the SCFI is 1 to 9;

administering lesional skin field therapy to the skin field of the subject.

Optionally, (i) when the skin field has an SCFI score of 20 to 30, the skin field is treated with field radiotherapy or the field application of a topical treatment; (ii) when the skin field has an SCFI of 10 to, the skin field is treated with the field application of a topical treatment; and (iii) when the skin field has an SCFI score of 1 to, the skin field is treated with a lesional therapy. In accordance with the rest of the specification, these statements also apply to scores of equivalent weighting.

Optionally, (i) when the skin field has an SCFI score of 26 to 30, the skin field is treated with field radiotherapy; (ii) when the skin field has an SCFI score of 20 to 25, the skin field is treated with field radiotherapy or the field application of a topical treatment; (iii) when the skin field has an SCFI of 10 to 19, the skin field is treated with the field application of a topical treatment; and (iv) when the skin field has an SCFI score of 1 to 9, the skin field is treated with a lesional therapy. In accordance with the rest of the specification, these statements also apply to scores of equivalent weighting.

Optionally, (i) when the skin field has an SCFI score of 26 to 30, the skin field is treated with field radiotherapy; (ii) when the skin field has an SCFI score of 24 or 25 and a 3 for the score of assessment (ii), the skin field is treated with field radiotherapy; (iii) when the skin field has an SCFI score of 20 to 25 but not a score of 24 or 25 with a 3 for the score of assessment (ii), the skin field is treated with field radiotherapy or the field application of a topical treatment; (iv) when the skin field has an SCFI of 10 to 19, the skin field is treated with the field application of a topical treatment; and (v) when the skin field has an SCFI score of 1 to 9, the skin field is treated with a lesional therapy. In accordance with the rest of the specification, these statements also apply to scores of equivalent weighting.

In some embodiments, the treatment results in an 80% or more improvement in the SCFI score and/or a SCFI score of less than 5. This is particularly the case where an appropriate treatment has been selected based on the SCFI score before treatment as discussed above. Optionally, the SCFI score before treatment is 15-30, 20-30, 25-30, 15-25, 15-20, or 20-25 and the SCFI after treatment is less than 5. Optionally, the SCFI score before treatment is 15-30, 20-30, 25-30, 15-25, 15-20, or 20-25 and the SCFI after treatment is reduced by 80% or more. For example, an initial score of 30 would reduce to a score of 6 or lower following treatment; an initial score of 25 would reduce to a score of 5 or lower following treatment; an initial score of 20 would reduce to a score of 4 or lower following treatment; and an initial score of 15 would reduce to a score of 3 or lower following treatment. In accordance with the rest of the specification, these statements also apply to scores of equivalent weighting.

Optionally, the SCFI score before treatment is 5-15, 5-10 or 10-15 and the SCFI after treatment is less than 5. Optionally, the SCFI score before treatment is 5-15, 5-10 or 10-15 and the SCFI after treatment is reduced by 80% or more. For example, an initial score of 15 would reduce to a score of 3 or lower following treatment; an initial score of 10 would reduce to a score of 2 or lower following treatment; and an initial score of 5 would reduce to a score of 1 or lower following treatment. In accordance with the rest of the specification, these statements also apply to scores of equivalent weighting.

The efficacy of the treatment is optionally evaluated about 2 weeks to 2 months after treatment is ceased, for example, 2 weeks, 4 weeks, 1 month, 6 weeks or 2 months after treatment is ceased, rather than at the end of treatment so that any potential confounding skin irritation is allowed to resolve before evaluation. The efficacy of the treatment is optionally evaluated at least 2 weeks, 4 weeks or 6 weeks after treatment is ceased.

In embodiments where the subject is treated, the treatment improved the clinical and/or subclinical skin damage and optionally the improvement is maintained for 3, 6, 9, 12, 18 or 24 months.

Several specific embodiments of the disclosure are set out below. In one embodiment, the present disclosure provides a method for assessing the severity of clinical or pre-clinical skin damage in at least one skin field in a subject comprising
- (i) assessing the number of keratoses in the skin field and assigning the skin field with a score based on the result of the assessment;
- (ii) assessing the thickness of the thickest keratosis in the skin field and assigning the skin field with a score based on the result of the assessment;
- (iii) assessing the proportion of the field affected by clinical or subclinical skin damage by assessing whether no area, 1-5% of the area, less than ⅓ of the area (or 6-33% of the area), ⅓-⅔ of the area (or 34-66% of the area), greater than ⅔ of the area to 95% of the area (or 67-95% of the area), or 96-100% of the area in the skin field is affected by clinical and/or pre-clinical skin damage and assigning the skin field with a score based on the result of the assessment; and assigning the skin field with a severity score based on the scores assigned in (i), (ii) and (iii), wherein the method does not involve the assessment of the subject's erythema.

In one embodiment, the present disclosure provides a method for assessing the severity of clinical or pre-clinical skin damage in at least one skin field in a subject comprising
- (i) assessing the number of keratoses in the skin field, categorizing the skin field into one of four categories consisting of no, mild, moderate, and severe keratoses, and assigning the skin field with a score based on the result of the assessment;
- (ii) assessing the thickness of the thickest keratosis in the skin field and assigning the skin field with a score based on the result of the assessment;
- (iii) assessing the proportion of the field affected by clinical or subclinical skin damage and assigning the skin field with a score based on the result of the assessment; and assigning the skin field with a severity score based on the scores assigned in (i), (ii) and (iii), wherein the method does not involve the assessment of the subject's erythema.

In one embodiment, the present disclosure provides a method for assessing the severity of clinical or pre-clinical skin damage in at least one skin field in a subject comprising
- (i) assessing the number of keratoses in the skin field and assigning the skin field with a score of 0-3 as follows:
- 0 for no discrete or continuous lesions;
- 1 for 1 to 5 discrete lesions in the skin field and no continuous keratoses;
- 2 for 6 to 15 discrete lesions in the skin field and no continuous keratoses; and
- 3 for continuous keratosis and/or more than 15 discrete lesions in the skin field;
- (ii) assessing the thickness of the thickest keratosis in the skin field and assigning the skin field with a score based on the result of the assessment;
- (iii) assessing the proportion of the field affected by clinical or subclinical skin damage and assigning the skin field with a score based on the result of the assessment; and assigning the skin field with a severity score based on the scores assigned in (i), (ii) and (iii). In accordance with the rest of the specification, these statements also apply to scores of equivalent weighting.

In one embodiment, the present disclosure provides a method for assessing the severity of clinical or pre-clinical skin damage in at least one skin field in a subject comprising
- (i) assessing the number of keratoses in the skin field and assigning the skin field with a score based on the result of the assessment;
- (ii) assessing the thickness of the thickest keratosis in the skin field and assigning the skin field with a score based on the result of the assessment;
- (iii) assessing the proportion of the field affected by clinical or subclinical skin damage and assigning the skin field with a of 0-5 as follows:
- 0 for no area affected;
- 1 for 1-5% of the area affected;
- 2 for less than ⅓ of the area affected (or 6-33% of the area);
- 3 for ⅓-⅔ of the area affected (or 34-66% of the area);
- 4 for greater than ⅔ of the area to 95% of the area affected (or 67-95% of the area), or
- 5 for 96-100% of the area in the skin field affected; and assigning the skin field with a severity score based on the scores assigned in (i), (ii) and (iii). In accordance with the rest of the specification, these statements also apply to scores of equivalent weighting.

In one embodiment, the present disclosure provides a method for assessing the severity of clinical or pre-clinical skin damage in at least one skin field in a subject comprising
- (i) assessing the number of keratoses in the skin field and assigning the skin field with a score of 0-3 as follows:
- 0 for no discrete or continuous lesions;
- 1 for 1 to 5 discrete lesions in the skin field and no continuous keratoses;
- 2 for 6 to 15 discrete lesions in the skin field and no continuous keratoses; and
- 3 for continuous keratosis and/or more than 15 discrete lesions in the skin field;
- (ii) assessing the thickness of the thickest keratosis in the skin field and assigning the skin field with a score based on the result of the assessment;
- (iii) assessing the proportion of the field affected by clinical or subclinical skin damage and assigning the skin field with a of 0-5 as follows:
- 0 for no area affected;
- 1 for 1-5% of the area affected;
- 2 for less than ⅓ of the area affected (or 6-33% of the area);
- 3 for ⅓-⅔ of the area affected (or 34-66% of the area);
- 4 for greater than ⅔ of the area to 95% of the area affected (or 67-95% of the area), or
- 5 for 96-100% of the area in the skin field affected; and assigning the skin field with a severity score based on the scores assigned in (i), (ii) and (iii). In accordance with the rest of the specification, these statements also apply to scores of equivalent weighting.

In one embodiment, the present disclosure provides a method for assessing the severity of clinical or pre-clinical skin damage in at least one skin field in a subject comprising
- (i) assessing the number of keratoses in the skin field and assigning the skin field with a score of 0-3 as follows:
- 0 for no discrete or continuous lesions;
- 1 for 1 to 5 discrete lesions in the skin field and no continuous keratoses;

2 for 6 to 15 discrete lesions in the skin field and no continuous keratoses; and 3 for continuous keratosis and/or more than 15 discrete lesions in the skin field;

(ii) assessing the thickness of the thickest keratosis in the skin field and assigning the skin field with a score a score of 0-3 as follows:

0 for no thickness;

1 for thin thickness, just perceptible thickness, or about 1 mm thick;

2 for moderate thickness, easily felt or seen thickness, or greater than 1 mm to about 3 mm thick; and 3 for very thick, cutaneous horns, or greater than 3 mm thick;

(iii) assessing the proportion of the field affected by clinical or subclinical skin damage and assigning the skin field with a of 0-5 as follows:

0 for no area affected;

1 for 1-5% of the area affected;

2 for less than ⅓ of the area affected (or 6-33% of the area);

3 for ⅓-⅔ of the area affected (or 34-66% of the area);

4 for greater than ⅔ of the area to 95% of the area affected (or 67-95% of the area), or 5 for 96-100% of the area in the skin field affected; and assigning the skin field with a severity score based on the scores assigned in (i), (ii) and (iii). In accordance with the rest of the specification, these statements also apply to scores of equivalent weighting.

The present disclosure also provides a method of treating clinical or pre-clinical skin damage in a subject in need thereof comprising selecting at least one skin field (i) assessing the number of keratoses in the skin field and assigning the skin field with a score based on the result of the assessment;

(ii) assessing the thickness of the thickest keratosis in the skin field and assigning the skin field with a score based on the result of the assessment;

(iii) assessing the proportion of the field affected by clinical or subclinical skin damage by assessing whether no area, 1-5% of the area, less than ⅓ of the area (or 6-33% of the area), ⅓-⅔ of the area (or 34-66% of the area), greater than ⅔ of the area to 95% of the area (or 67-95% of the area), or 96-100% of the area in the skin field is affected by clinical and/or pre-clinical skin damage and assigning the skin field with a score based on the result of the assessment; and, based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy, wherein the method does not involve the assessment of the subject's erythema.

The present disclosure also provides a method of treating clinical or pre-clinical skin damage in a subject in need thereof comprising selecting at least one skin field (i) assessing the number of keratoses in the skin field, categorizing the skin field into one of four categories consisting of no, mild, moderate, and severe keratoses, and assigning the skin field with a score based on the result of the assessment;

(ii) assessing the thickness of the thickest keratosis in the skin field and assigning the skin field with a score based on the result of the assessment;

(iii) assessing the proportion of the field affected by clinical or subclinical skin damage and assigning the skin field with a score based on the result of the assessment; and, based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy, wherein the method does not involve the assessment of the subject's erythema.

The present disclosure also provides a method of treating clinical or pre-clinical skin damage in a subject in need thereof comprising selecting at least one skin field (i) assessing the number of keratoses in the skin field and assigning the skin field with a score of 0-3 as follows:

0 for no discrete or continuous lesions;

1 for 1 to 5 discrete lesions in the skin field and no continuous keratoses;

2 for 6 to 15 discrete lesions in the skin field and no continuous keratoses; and 3 for continuous keratosis and/or more than 15 discrete lesions in the skin field;

(ii) assessing the thickness of the thickest keratosis in the skin field and assigning the skin field with a score based on the result of the assessment;

(iii) assessing the proportion of the field affected by clinical or subclinical skin damage and assigning the skin field with a score based on the result of the assessment; and, based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy. In accordance with the rest of the specification, these statements also apply to scores of equivalent weighting.

The present disclosure also provides a method of treating clinical or pre-clinical skin damage in a subject in need thereof comprising selecting at least one skin field (i) assessing the number of keratoses in the skin field and assigning the skin field with a score based on the result of the assessment;

(ii) assessing the thickness of the thickest keratosis in the skin field and assigning the skin field with a score based on the result of the assessment;

(iii) assessing the proportion of the field affected by clinical or subclinical skin damage and assigning the skin field with a of 0-5 as follows:

0 for no area affected;

1 for 1-5% of the area affected;

2 for less than ⅓ of the area affected (or 6-33% of the area);

3 for ⅓-⅔ of the area affected (or 34-66% of the area);

4 for greater than ⅔ of the area to 95% of the area affected (or 67-95% of the area), or 5 for 96-100% of the area in the skin field affected; and, based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy. In accordance with the rest of the specification, these statements also apply to scores of equivalent weighting.

The present disclosure also provides a method of treating clinical or pre-clinical skin damage in a subject in need thereof comprising selecting at least one skin field
  (i) assessing the number of keratoses in the skin field and assigning the skin field with a score of 0-3 as follows:
  0 for no discrete or continuous lesions;
  1 for 1 to 5 discrete lesions in the skin field and no continuous keratoses;
  2 for 6 to 15 discrete lesions in the skin field and no continuous keratoses; and
  3 for continuous keratosis and/or more than 15 discrete lesions in the skin field;
  (ii) assessing the thickness of the thickest keratosis in the skin field and assigning the skin field with a score based on the result of the assessment;
  (iii) assessing the proportion of the field affected by clinical or subclinical skin damage and assigning the skin field with a of 0-5 as follows:
  0 for no area affected;
  1 for 1-5% of the area affected;
  2 for less than ⅓ of the area affected (or 6-33% of the area);
  3 for ⅓-⅔ of the area affected (or 34-66% of the area);
  4 for greater than ⅔ of the area to 95% of the area affected (or 67-95% of the area), or
  5 for 96-100% of the area in the skin field affected; and, based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy. In accordance with the rest of the specification, these statements also apply to scores of equivalent weighting.

The present disclosure also provides a method of treating clinical or pre-clinical skin damage in a subject in need thereof comprising selecting at least one skin field
  (i) assessing the number of keratoses in the skin field and assigning the skin field with a score of 0-3 as follows:
  0 for no discrete or continuous lesions;
  1 for 1 to 5 discrete lesions in the skin field and no continuous keratoses;
  2 for 6 to 15 discrete lesions in the skin field and no continuous keratoses; and
  3 for continuous keratosis and/or more than 15 discrete lesions in the skin field;
  (ii) assessing the thickness of the thickest keratosis in the skin field and assigning the skin field with a score a score of 0-3 as follows:
  0 for no thickness;
  1 for thin thickness, just perceptible thickness, or about 1 mm thick;
  2 for moderate thickness, easily felt or seen thickness, or greater than 1 mm to about 3 mm thick; and
  3 for very thick, cutaneous horns, or greater than 3 mm thick;
  (iii) assessing the proportion of the field affected by clinical or subclinical skin damage and assigning the skin field with a of 0-5 as follows:
  0 for no area affected;
  1 for 1-5% of the area affected;
  2 for less than ⅓ of the area affected (or 6-33% of the area);
  3 for ⅓-⅔ of the area affected (or 34-66% of the area);
  4 for greater than ⅔ of the area to 95% of the area affected (or 67-95% of the area), or
  5 for 96-100% of the area in the skin field affected; and, based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy. In accordance with the rest of the specification, these statements also apply to scores of equivalent weighting.

Aspects of the Disclosure Having a Global Score

In another aspect, the present disclosure provides a method of assessing the severity of clinical or pre-clinical skin damage in at least one skin field in a subject comprising assessing the severity of the skin damage in the skin field and allocating that skin field into 1 of five categories of increasing severity of skin damage based on the severity of the skin and assigning a global score to the skin field based on the categorization.

Optionally, the five categories are unaffected, mild skin field damage, moderate skin field damage, severe skin field damage, and very severe skin field damage. Optionally, the global score assigned to these categories are 0, 1, 2, 3 and 4 respectively.

Optionally, prior to the assessment, the assessor is trained and/or provided with instructions to categorize the skin field into one of five categories of increasing severity of skin damage and assign the score associated with that category. Optionally, the assessor is trained and/or provided with instructions that the categories are unaffected, mild skin field damage, moderate skin field damage, severe skin field damage, and very severe skin field damage. Optionally, the assessor is trained and/or provided with instructions that the global score assigned to these categories is 0, 1, 2, 3 and 4 respectively. Optionally, the assessment is qualitative not quantitative. Optionally, no subtests are conducted to determine how to classify the skin field. Optionally, there is no assessment of the percentage area affected within the skin field (i.e. no quantitative assessment of the affected area). Optionally, there is no assessment of hyperkeratosis and/or no assessment of sun damage severity. Optionally, the assessment is performed on one or more image of the skin field. Optionally, the one or more images of the skin field are obtained prior to the assessment.

In an alternative aspect, the method is of assessing the severity of clinical or pre-clinical skin damage in at least one skin field in a subject comprising
  (i) assessing the skin field as having:
    a) no keratosis evident;
    b) a small area of affected with few or thin keratoses;
    c) patchy involvement in the zone, moderately thick keratosis, or patchy involvement in the zone with moderately thick keratosis;
    d) extensive involvement of the zone, numerous thicker keratosis, or extensive involvement of the zone with numerous thicker keratoses;
    e) extensive involvement of the zone with (A) numerous thicker keratosis with cutaneous horn; and/or (B) confluent (ie continuous) keratoses, or
    f) near complete involvement of the zone with numerous thicker keratosis.

Optionally, the method further comprises (ii) assigning the skin field a global score based on the results of assessment (i). Optionally, the assessment is performed on one or more image of the skin field. Optionally, the one or more images of the skin field are obtained prior to the assessment.

In another alternative aspect, the present disclosure provides a non-invasive method for collecting data useful for determining severity of clinical or preclinical skin damage in at least one skin field in a subject, the method comprising:
(i) assessing the skin field as having:
   a) no keratosis evident;
   b) a small area of affected with few or thin keratoses;
   c) patchy involvement in the zone, moderately thick keratosis, or patchy involvement in the zone with moderately thick keratoses;
   d) extensive involvement of the zone, numerous thicker keratosis, or extensive involvement of the zone with numerous thicker keratoses; or
   e) extensive involvement of the zone with (A) numerous thicker keratosis with cutaneous horn; and/or (B) confluent (ie continuous) keratoses, or
   f) near complete involvement of the zone with numerous thicker keratosis.

Optionally, the method further comprises (ii) assigning the skin field a global score based on the results of assessment (i). Optionally, the assessment is performed on one or more image of the skin field. Optionally, the one or more images of the skin field are obtained prior to the assessment.

In another aspect, the present disclosure provides a method of assessing the severity of clinical or pre-clinical skin damage in at least one skin field in a subject comprising
(i) assessing the skin field as having:
   a) no keratosis evident;
   b) a small area affected with few or thin keratoses;
   c) patchy involvement in the zone with moderately thick keratoses;
   d) extensive involvement of the zone with numerous thicker keratoses;
   e) extensive involvement of the zone with (A) numerous thicker keratosis with cutaneous horn; and/or (B) confluent (ie continuous) keratoses, or
   f) near complete involvement of the zone with numerous thicker keratoses; and
(ii) assigning the skin field a global score based on the results of assessment (i). Alternatively, the present disclosure provides a method of assessing the severity of clinical or pre-clinical skin damage in at least one skin field in a subject comprising
(i) assessing the skin field as having:
   a) no keratosis evident;
   b) a small area affected with few or thin keratoses;
   c) patchy involvement in the zone, moderately thick keratosis, or patchy involvement in the zone with moderately thick keratoses;
   d) extensive involvement of the zone, numerous thicker keratosis, or extensive involvement of the zone with numerous thicker keratoses;
   e) extensive involvement of the zone with (A) numerous thicker keratosis with cutaneous horn; and/or (B) confluent (ie continuous) keratoses, or
   f) near complete involvement of the zone with numerous thicker keratoses; and
(ii) assigning the skin field a global score based on the results of assessment (i).

Optionally, the global score assigned to these categories are 0 for (a), 1 for (b), 2 for (c), 3 for (d) and 4 for (e) or (f) respectively. Optionally, the assessment is performed on one or more images of the skin field. Optionally, the one or more images of the skin field are obtained prior to the assessment.

In another aspect, the present disclosure provides a method of assessing the severity of clinical or pre-clinical skin damage in at least one skin field in a subject comprising
(i) selecting an assessor trained to assess the skin field as having:
   a) no keratosis evident;
   b) a small area affected with few or thin keratoses;
   c) patchy involvement in the zone, moderately thick keratosis, or patchy involvement in the zone with moderately thick keratoses;
   d) extensive involvement of the zone, numerous thicker keratosis, or extensive involvement of the zone with numerous thicker keratoses;
   e) extensive involvement of the zone with (A) numerous thicker keratosis with cutaneous horn; and/or (B) confluent (ie continuous) keratoses; or
   f) near complete involvement of the zone with numerous thicker keratoses; and
(ii) the assessor assessing the one or more skin field in accordance with their training. Alternatively, the disclosure provides a method of assessing the severity of clinical or pre-clinical skin damage in at least one skin field in a subject comprising
(i) selecting an assessor trained to assess the skin field as having:
   a) no keratosis evident;
   b) a small area affected with few or thin keratoses;
   c) patchy involvement in the zone with moderately thick keratoses;
   d) extensive involvement of the zone with numerous thicker keratoses;
   e) extensive involvement of the zone with (A) numerous thicker keratosis with cutaneous horn; and/or (B) confluent (ie continuous) keratoses, or
   f) near complete involvement of the zone with numerous thicker keratoses; and
(ii) the assessor assessing the one or more skin field in accordance with their training, and
(iii) assigning the skin field a global score based on the results of assessment (i). Alternatively, the disclosure provides a method of assessing the severity of clinical or pre-clinical skin damage in at least one skin field in a subject comprising
(i) selecting an assessor trained to assess the skin field as having:
   a) no keratosis evident;
   b) a small area affected with few or thin keratoses;
   c) patchy involvement in the zone, moderately thick keratosis, or patchy involvement in the zone with moderately thick keratoses;
   d) extensive involvement of the zone, numerous thicker keratosis, or extensive involvement of the zone with numerous thicker keratoses;
   e) extensive involvement of the zone with (A) numerous thicker keratosis with cutaneous horn; and/or (B) confluent (i.e. continuous) keratoses, or
   f) near complete involvement of the zone with numerous thicker keratoses; and
(ii) the assessor assessing the one or more skin field in accordance with their training, and
(iii) assigning the skin field a global score based on the results of assessment (i). Optionally, the assessment is performed on one or more image of the skin field. Optionally, the one or more images of the skin field are obtained prior to the assessment.

In another aspect, the present disclosure provides a method for monitoring the response of a subject to treatment for clinical or pre-clinical skin damage, the method comprising (i) prior to the subject receiving treatment assessing the skin field as having:
  b) a small area affected with few or thin keratoses;
  c) patchy involvement in the zone, moderately thick keratosis, or patchy involvement in the zone with moderately thick keratoses;
  d) extensive involvement of the zone, numerous thicker keratosis, or extensive involvement of the zone with numerous thicker keratoses; or
  e) extensive involvement of the zone with (A) numerous thicker keratosis with cutaneous horn; and/or (B) confluent (ie continuous) keratoses, or
  f) near complete involvement of the zone with numerous thicker keratoses; and
(ii) after the subject receiving treatment assessing the skin field as having:
  a) no keratosis evident;
  b) a small area of affected with few or thin keratoses;
  c) patchy involvement in the zone, moderately thick keratosis, or patchy involvement in the zone with moderately thick keratoses;
  d) extensive involvement of the zone, numerous thicker keratosis, or extensive involvement of the zone with numerous thicker keratoses; or
  e) extensive involvement of the zone with (A) numerous thicker keratosis with cutaneous horn; and/or (B) confluent (ie continuous) keratoses, or
  f) near complete involvement of the zone with numerous thicker keratosis;

and comparing the assessment of i) and ii) to monitor the subject's response to the treatment. Optionally, a decrease in the severity of the assessment of (ii) as compared to the assessment of (i) is indicative of the subject responding to the treatment, and/or is indicative of improvement resulting from the treatment in the clinical and/or pre-clinical skin damage. Optionally, the assessment is performed on one or more image of the skin field. Optionally, the one or more images of the skin field are obtained prior to the assessment. In embodiments where a global score is assigned (as described below), optionally a decrease in the global score assigned following the assessment of (ii) as compared to the global score assigned following the assessment of (i) is indicative of the subject responding to the treatment, and/or is indicative of improvement resulting from the treatment in the clinical and/or pre-clinical skin damage In a further aspect, the present disclosure provides a method for monitoring the response of a subject to treatment for clinical or pre-clinical skin damage, the method comprising
(i) assessing the skin field as having:
  b) a small area affected with few or thin keratoses;
  c) patchy involvement in the zone, moderately thick keratosis, or patchy involvement in the zone with moderately thick keratoses;
  d) extensive involvement of the zone, numerous thicker keratosis, or extensive involvement of the zone with numerous thicker keratoses; or
  e) extensive involvement of the zone with (A) numerous thicker keratosis with cutaneous horn; and/or (B) confluent (ie continuous) keratoses, or
  f) near complete involvement of the zone with numerous thicker keratoses; and
(ii) treating the skin field based on the assessment of the skin field, and
(iii) following treatment repeating the assessments in (i) and comparing the initial and repeated assessments to monitor the subject's response to the treatment.

Optionally, the assessment is performed on one or more image of the skin field. Optionally, the one or more images of the skin field are obtained prior to the assessment.

Optionally, the global score assigned to these categories are 0 for (a), 1 for (b), 2 for (c), 3 for (d) and 4 for (e) or (f) respectively.

Optionally, following assigning the global score the subject is treated by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy.

In the five preceding aspects of the disclosure, optionally, prior to the assessment, the assessor is instructed to categorize the skin field into one of five categories of increasing severity of skin damage and assign the score associated with that category. Optionally, the assessor is advised that the categories are
 1. no keratosis evident;
 2. a small area affected with few or thin keratoses;
 3. patchy involvement in the zone, moderately thick keratosis, or patchy involvement in the zone with moderately thick keratoses;
 4. extensive involvement of the zone, numerous thicker keratosis, or extensive involvement of the zone with numerous thicker keratoses;
 5. extensive involvement of the zone with (A) numerous thicker keratosis with cutaneous horn; and/or (B) confluent (ie continuous) keratoses; or near complete involvement of the zone with numerous thicker keratoses.

Optionally, the assessor is advised that the global score assigned to these categories are 0, 1, 2, 3 and 4 respectively. Optionally, the assessment is qualitative not quantitative. Optionally, no subtests are conducted to determine how to classify the skin field. Optionally, there is no assessment of the percentage area affected within the skin field (ie no quantitative assessment of the affected area). Optionally, there is no assessment of hyperkeratosis and/or no assessment of sun damage severity.

The assessor is optionally a trained medical professional or an artificial intelligence. The medical professional can be a general practitioner, dermatologist, oncologist, radiologist or nurse. Optionally, the nurse is a dermatology, oncology or radiology nurse.

The global assessment is made by assessing one or more images of the skin. As for the multistep assessments, the global assessment is optionally determined from one or more physical or electronic photographs, videos, scans (including 3D scans such as a CT scan) or other images of the skin. The images can be physical, such as printed, or electronic. Optionally, there are multiple still images such as photographs from different angles. However, a single photograph has been shown to be effective so long as it is close enough and of sufficient quality to properly visualize the skin damage. A suitable image is optionally isolated from a video. The video can be recorded or streamed to the assessor.

The assessment of the subject's skin may involve visual assessment or dermoscopic analysis, analysis of one or more image of the subject's skin, reference to one or more biopsy (histopathology) results for one or more of the subject's lesions, and/or reference to the subject's medical history (such as a prior skin cancer diagnosis). In some embodiments, assessment is performed by a computer program. For example, the visual assessment, photographic analysis, reference to biopsy results, reference to histopathology results and/or reference to the subject's medical history is optionally conducted by a computer program. Programs using AI to assess the severity of actinic keratosis have been developed and are expected to be adaptable to conduct the assessment of this disclosure and inform the user regarding the severity of a skin field and/or the suitable treatment.

In some embodiments, the skin field is further assessed for the presence of cancer in the skin field and/or a histologically proven history of cancer in the skin field within the past 6 months.

In some embodiments, the method does not involve the assessment of the subject's erythema.

In some embodiments, two or more skin fields are assessed on one subject. Optionally, two or more skin fields are assessed on one subject and a separate score allocated for each field.

In some embodiments, the subject has a global score of 3 or 4 (or a category of (d) or (e) or (f) as described in relation to the aspects of the disclosure having a global score above) and is treated with a skin field therapy. More specifically, the skin field therapy is recommended at least in part because the global score is 3 or 4 (or the skin field is category of (d) or (e) as described in relation to the aspects of the disclosure having a global score above). The skin field therapies are as described in relation to the multistep assessment aspects of the disclosure.

In some embodiments, the subject is assigned a global score of 4 (or a category of (e) or (f) as described in relation to the aspects of the disclosure having a global score above) and is treated with field radiation therapy. In other embodiments, the subject is assigned a global score of 3 (or a category of (d) as described in relation to the aspects of the disclosure having a global score above) and is treated with either field radiation therapy or the field application of a topical treatment. In alternate embodiments, the subject is assigned a global score of 2 (or a category of (c) as described in relation to the aspects of the disclosure having a global score above) and is treated with either the field application of a topical treatment or a lesional therapy. In other embodiments, the subject is assigned a global score of 1 (or a category of (b) as described in relation to the aspects of the disclosure having a global score above) and is treated with a lesional therapy.

In some embodiments, wherein
(i) when the subject is assigned a global score of 4 (or assessed as category (e) or (f)), the subject is treated with field radiotherapy;
(ii) when the subject is assigned a global score of 3 (or assessed as category (d)), the subject is treated with field radiotherapy or the field application of a topical treatment;
(iii) when the subject is assigned a global score of 2 (or assessed as category (c)), the subject is treated with the field application of a topical treatment or lesional therapy; and
(iv) when the subject is assigned a global score of 1 (or assessed as category (b)), the subject is treated with lesional therapy.

Optionally, the treatment of the subject's clinical or preclinical skin damage prevents the development of skin cancer or further skin cancers. Alternatively, or additionally, the treatment reduces the clinical and/or pre-clinical skin damage in the skin field.

In some embodiments, the subject has (a) a global score of 3 or 4 (or is assessed as category of (d) or (e) or (f) as described in relation to the aspects of the disclosure having a global score above), and (b) the skin field includes 1 or more cancerous lesions. There are simultaneous cancerous lesions when there are two or more cancerous lesions occurring in the skin field at the same time. In those embodiments, the subject is optionally treated with (i) radiation therapy including one or more lesional tumorcidal radiation therapy boosts to treat the cancerous lesions, or (ii) surgical removal of the cancerous lesions followed by field radiation therapy.

In some embodiments, the subject has a global score of 1 or 2 (or is assessed as category of (b) or (c) as described in relation to the aspects of the disclosure having a global score above) and is treated with a lesional therapy. Optionally, the lesional therapy is (a) freezing one or more lesions with liquid nitrogen, (b) shaving, curetting or surgically removing one or more lesions, or (c) applying a topical treatment to one or more lesions. Optionally, the topical treatment is 5-fluorouracil, imiquimod, ingenol mebutate, diclofenac or photodynamic therapy. The topical treatment is applied to one or more lesions.

In some embodiments, the subject has a global score of 1 or 2 (or is assessed as category of (b) or (c) as described in relation to the aspects of the disclosure having a global score above) and the skin field includes 3 or more simultaneous cancerous lesions.

In these embodiments, the patient is optionally treated with a field therapy. Optionally, the patient is treated with radiation therapy including one or more lesional tumorcidal radiation therapy boosts to treat the cancerous lesions, or surgical removal of the cancerous lesions followed by field radiation therapy.

In some embodiments, the skin field is further assessed for the presence of cancer in the skin field and/or a histologically proven history of cancer in the skin field within the past 6 months. Optionally, where the global score for the skin field is 1 or 2 (preferably 2) (or is assessed as category of (b) or (c) as described in relation to the aspects of the disclosure having a global score above) and the skin field is assessed as (i) including skin cancer, or (ii) having a histologically proven history of cancer, then the treatment provided to the subject is a skin field treatment. Optionally, the patient is treated with radiation therapy including one or more lesional tumorcidal radiation therapy boosts to treat the cancerous lesions, or surgical removal of the cancerous lesions followed by field radiation therapy.

In some embodiments, the treatment results in an improvement in the global score and/or a global score of less than 2 (or a category of (a) or (b) as described in relation to the aspects of the disclosure having a global score above). This is particularly the case where an appropriate treatment has been selected based on the global score before treatment as discussed above. Optionally, the global score before treatment is 3 or 4 (or category of (d) or (e) or (f) as described in relation to the aspects of the disclosure having a global score above) and the global after treatment is 0 or 1 (or category of (a) or (b) as described in relation to the aspects of the disclosure having a global score above).

The efficacy of the treatment is optionally evaluated about 2 weeks to 2 months after treatment is ceased, for example, 2 weeks, 4 weeks, 1 month, 6 weeks or 2 months after treatment is ceased, rather than at the end of treatment so that any potential confounding skin irritation is allowed to resolve before evaluation. The efficacy of the treatment is optionally evaluated at least 2 weeks, 4 weeks or 6 weeks after treatment is ceased.

In embodiments where the subject is treated, the treatment improved the clinical and/or subclinical skin damage and optionally the improvement is maintained for 3, 6, 9, 12, 18 or 24 months.

The present disclosure also provides a method of administering a skin field treatment to a subject comprising confirming that the subject is in need of a skin field treatment by:
(i) assessing the skin field for:
b) a small area affected with few or thin keratoses;
c) patchy involvement in the zone, moderately thick keratosis, or patchy involvement in the zone with moderately thick keratoses;
d) extensive involvement of the zone, numerous thicker keratosis, or extensive involvement of the zone with numerous thicker keratoses; or
e) extensive involvement of the zone with (A) numerous thicker keratosis with cutaneous horn; and/or (B) confluent (i.e. continuous) keratoses, or
f) near complete involvement of the zone with numerous thicker keratoses; and
(ii) confirming the skin field is category (c), (d), (e) or (f); and administering field radiation therapy to the skin field of the subject. Optionally, the method confirms in step (ii) that the skin field is category (d), (e) or (f).

The present disclosure also provides a method for treating clinical or pre-clinical skin damage in at least one skin field in a subject wherein the skin field has been categorized as determined by a process comprising the steps of:
(i) selecting and assessing at least one skin field for:
b) a small area affected with few or thin keratoses;
c) patchy involvement in the zone with moderately thick keratoses;
d) extensive involvement of the zone with numerous thicker keratoses;
e) extensive involvement of the zone with (A) numerous thicker keratosis with cutaneous horn; and/or (B) confluent (i.e. continuous) keratoses, or
f) near complete involvement of the zone with numerous thicker keratoses; and
(ii) optionally a global score of 1 for (b), 2 for (c), 3 for (d) and 4 for (e) or (f) respectively has been assigned to the skin field,
the method for treating comprising
treating the skin field with a field therapy when the skin field is category d), e) orf);
treating the skin field with a lesional therapy when the skin field is category b); or
treating the skin field with a field or lesional therapy when the skin field is category c).

Alternatively, the present disclosure provides a method for treating clinical or pre-clinical skin damage in at least one skin field in a subject, the method comprising the steps of:
(i) selecting and assessing at least one skin field for:
b) a small area affected with few or thin keratoses;
c) patchy involvement in the zone with moderately thick keratoses;
d) extensive involvement of the zone with numerous thicker keratoses;
e) extensive involvement of the zone with (A) numerous thicker keratosis with cutaneous horn; and/or (B) confluent (ie continuous) keratoses, or
f) near complete involvement of the zone with numerous thicker keratoses; and
(ii) optionally assigning a global score of 1 for (b), 2 for (c), 3 for (d) and 4 for (e) or (f) respectively,
(iii) treating the clinical or pre-clinical skin damage, wherein
treating the skin field with a field therapy when the skin field is category d), e) orf);
treating the skin field with a lesional therapy when the skin field is category b); or
treating the skin field with a field or lesional therapy when the skin field is category c).

The present disclosure also provides a method of administering radiation treatment to a subject comprising confirming that the subject is in need of radiation treatment by:
(i) assessing the skin field for:
b) a small area affected with few or thin keratoses;
c) patchy involvement in the zone, moderately thick keratosis, or patchy involvement in the zone with moderately thick keratoses;
d) extensive involvement of the zone, numerous thicker keratosis, or extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratoses; and
(ii) confirming the skin field is category (d), (e) or (f); and administering field radiation therapy to the skin field of the subject. Optionally, the method confirms in step (ii) that the skin field is category (e) or (f).

The present disclosure also provides a method of administering a topical skin field treatment to a subject comprising confirming that the subject is in need of a topical skin field treatment by:
(i) assessing the skin field for:
b) a small area affected with few or thin keratoses;
c) patchy involvement in the zone, moderately thick keratosis, or patchy involvement in the zone with moderately thick keratoses;
d) extensive involvement of the zone, numerous thicker keratosis, or extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratoses; and
(ii) confirming the skin field is category (c) or (d); and administering topical skin field therapy to the skin field of the subject.

The present disclosure also provides a method of administering a lesional skin field treatment to a subject comprising confirming that the subject is in need of a lesional skin field treatment by:
(i) assessing the skin field for:
b) a small area affected with few or thin keratoses;
c) patchy involvement in the zone, moderately thick keratosis, or patchy involvement in the zone with moderately thick keratoses;
d) extensive involvement of the zone, numerous thicker keratosis, or extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratoses; and
(ii) confirming the skin field is category (b) or (c); and administering lesional skin field therapy to the skin field of the subject. Optionally, the method confirms in step (ii) that the skin field is category (b).

The present disclosure also provides a method for administering radiation therapy in at least one skin field in a subject wherein the skin field has been categorized as determined by a process comprising the steps of:
(i) selecting and assessing at least one skin field for:
g) a small area affected with few or thin keratoses;
h) patchy involvement in the zone with moderately thick keratoses;
i) extensive involvement of the zone with numerous thicker keratoses;
j) extensive involvement of the zone with (A) numerous thicker keratosis with cutaneous horn; and/or (B) confluent (i.e. continuous) keratoses, or
k) near complete involvement of the zone with numerous thicker keratoses; and
(ii) optionally a global score of 1 for (b), 2 for (c), 3 for (d) and 4 for (e) or (f) respectively has been assigned to the skin field,
the method for treating comprising
treating the skin field with radiation therapy when the skin field is category d), e) or f). Optionally, the method confirms in step (ii) that the skin field is category (e) or (f).

The present disclosure also provides a method for administering topical therapy in at least one skin field in a subject wherein the skin field has been categorized as determined by a process comprising the steps of:
(i) selecting and assessing at least one skin field for:
b) a small area affected with few or thin keratoses;
c) patchy involvement in the zone with moderately thick keratoses;
d) extensive involvement of the zone with numerous thicker keratoses;
e) extensive involvement of the zone with (A) numerous thicker keratosis with cutaneous horn; and/or (B) confluent (i.e. continuous) keratoses, or
f) near complete involvement of the zone with numerous thicker keratoses; and
(ii) optionally a global score of 1 for (b), 2 for (c), 3 for (d) and 4 for (e) or (f) respectively has been assigned to the skin field,
the method for treating comprising
treating the skin field with a topical therapy when the skin field is category c) or d).

The present disclosure also provides a method for administering lesional therapy in at least one skin field in a subject wherein the skin field has been categorized as determined by a process comprising the steps of:
(i) selecting and assessing at least one skin field for:
b) a small area affected with few or thin keratoses;
c) patchy involvement in the zone with moderately thick keratoses;
d) extensive involvement of the zone with numerous thicker keratoses;
e) extensive involvement of the zone with (A) numerous thicker keratosis with cutaneous horn; and/or (B) confluent (i.e. continuous) keratoses, or
f) near complete involvement of the zone with numerous thicker keratoses; and
(ii) optionally a global score of 1 for (b), 2 for (c), 3 for (d) and 4 for (e) or (f) respectively has been assigned to the skin field,
the method for treating comprising
treating the skin field with a lesional therapy when the skin field is category b) or c). Optionally, the skin field is category b).

Skin Fields

The following embodiments of the skin field are applicable to all aspects of the disclosure.

Optionally, the at least one skin field is an anatomical region of skin. Alternatively, the skin field is not anatomical such as part of an arm or leg. Where the skin field is not anatomical it needs to be defined in advance of the assessment, preferably in a manner that is reproducible such that the field can be reproduced to assess the efficacy of treatment.

Optionally, the at least one skin field is selected from the group consisting of head, scalp (optionally divided into the occipital, right and left temporal and vertex of the scalp), tonsure of the scalp (an area bordered by the hair line such as a balding spot), forehead (ie the upper third of the face), nose (optionally the right and left halves), right cheek (optionally divided into the lower and upper right cheek), left cheek (optionally divided into the lower and upper left cheek), right ear (optionally anterior and posterior right ear), left ear (anterior and posterior left ear), neck (optionally divided into the back of the neck and front of the neck), chin, right forearm, left forearm, dorsum of the right hand, dorsum of the left hand, palm of the left hand, palm of the right hand, right lower leg, left lower leg, right upper leg, left upper leg, dorsum of the right foot, dorsum of the left foot, sole of the right foot, sole of the left foot, back (optionally the upper and lower back are considered separate fields), shoulders (optionally the right shoulder, left shoulder or across the top of the upper back), chest (optionally the upper chest and lower chest are considered separate fields), chest from the waist up, back from the waist up, abdomen, buttocks (optionally the right buttock and left buttock are considered separate fields), right upper arm, left upper arm, décolletage, or combinations thereof including combinations of portions thereof, such as the lower and upper left and/or right arm, the lower and upper left and/or right leg, the right cheek and right ear, the left cheek and left ear, the right cheek and right half of the forehead and optionally also the right ear and/or right half of the nose, the right half of the face, left cheek and left half of the forehead and optionally also the left ear and/or left half of the nose, the left half of the face, the chin and lower left and right cheeks (ie the lower third of the face), the nose and upper right and left cheeks (ie the middle third of the face), and the nose, upper right and left cheeks, and right and left ears.

Alternatively, the at least one skin field is selected from the group consisting of head, scalp, occipital scalp, right temporal scalp, left temporal scalp, vertex of the scalp, tonsure of the scalp, forehead, nose, right cheek, left cheek, right ear, anterior right ear, posterior right ear, anterior left ear, posterior left ear, left ear, neck, back of the neck, front of the neck, right forearm, left forearm, dorsum of the right hand, dorsum of the left hand, right lower leg, left lower leg, right upper leg, left upper leg, dorsum of the right foot, dorsum of the left foot, right shoulder, left shoulder, upper back, lower back, central upper back, right shoulder, left shoulder, upper chest, lower chest, right upper arm, left upper arm, décolletage, or combinations thereof including combinations of portions thereof, such as the lower and upper left and/or right arm, the lower and upper left and/or right leg, the right cheek and right ear, the left cheek and left ear, the right cheek and right half of the forehead and optionally also the right ear and/or right half of the nose, the right half of the face, left cheek and left half of the forehead and optionally also the left ear and/or left half of the nose, and the left half of the face.

Alternatively, the at least one skin field is selected from the group consisting of scalp, tonsure of the scalp, forehead, nose, right cheek, left cheek, right ear, left ear, front of the neck, back of the neck, right forearm, left forearm, dorsum of the right hand, dorsum of the left hand, dorsum of the right foot, dorsum of the left foot, right lower leg, left lower leg, right shoulder, left shoulder, upper chest, and upper back.

Alternatively, the at least one skin field is selected from the group consisting of scalp, tonsure of the scalp, forehead, nose, right cheek, left cheek, right ear, left ear, right forearm, left forearm, dorsum of the right hand, dorsum of the left hand, right lower leg, left lower leg, right shoulder, left shoulder, upper chest, and upper back.

Alternatively, the at least one skin field is selected from the group consisting of head, scalp, forehead, nose, right cheek, left cheek, right ear, left ear, neck (optionally divided into the back of the neck and front of the neck), or combinations thereof including combinations of portions thereof, such as the right cheek and right ear, the left cheek and left ear, the right cheek and right half of the forehead, the right cheek and right half of the forehead and the right ear, the right cheek and right half of the forehead and the right half of the nose, the right cheek and right half of the forehead and the right ear and the right half of the nose, the right half of the face, left cheek and left half of the forehead, the left cheek and left half of the forehead and the left ear, the left cheek and left half of the forehead and the left half of the nose, the left cheek and left half of the forehead and the left ear and the left half of the nose, and the left half of the face.

Alternatively, the at least one skin field is selected from the group consisting of scalp, forehead, nose, right cheek, left cheek, right ear, left ear, and neck. Preferably, the at least one skin field is selected from the group consisting of the lower third of the face, the middle third of the face, the upper third of the face, the middle third of the face combined with the ears, the ears, the tonsure of the scalp, the front of the neck and the back of the neck.

Alternatively, the at least one skin field is selected from the group consisting of right forearm, left forearm, dorsum of the right hand, dorsum of the left hand, right upper leg, left upper leg, right lower leg, left lower leg, dorsum of the right foot, dorsum of the left foot, right upper arm, left upper arm, or combinations thereof including the lower and upper left and/or right leg, lower and upper left and/or right arm, the right forearm and dorsum of the right hand, the left forearm and dorsum of the left hand, lower leg and dorsum of the foot on the right or left.

Alternatively, the at least one skin field is selected from the group consisting of back (optionally the upper and lower back are considered separate fields, alternatively the back is divided into upper, middle and lower back fields, optionally divided the central upper back is considered a separate field from the right and left shoulders), shoulders (optionally the right shoulder, left shoulder or across the top of the upper back), chest (optionally the upper chest and lower chest are considered separate fields), chest from the waist up, back from the waist up, décolletage, or combinations thereof.

In some embodiments, the skin field is a minimum of 25 $cm^2$ in area. In some embodiments, the skin field is a maximum of 1,000 $cm^2$ in area. Optionally, the skin field is between 25 $cm^2$ and 1,000 $cm^2$ in area. Alternatively, the skin field is between 50 $cm^2$ and 1,000 $cm^2$ in area, 100 $cm^2$ and 1,000 $cm^2$ in area, 100 $cm^2$ and 500 $cm^2$, or 500 $cm^2$ and 1,000 $cm^2$ in area. Alternatively, the skin field is between 25 $cm^2$ and 900 $cm^2$ in area, 25 $cm^2$ and 500 $cm^2$ in area, 50 $cm^2$ and 900 $cm^2$, or 100 $cm^2$ and 900 $cm^2$ in area.

Further Embodiments

The following embodiments are applicable to all aspects of the disclosure.

Optionally, the skin damage is clinical.

The clinical or pre-clinical skin damage is optionally pre-cancerous, cancerous or a combination thereof. For example, the cancerous skin has non-melanoma skin cancer.

Optionally, the clinical or pre-clinical skin damage is actinic keratosis, Bowenoid keratosis, Bowen's disease, skin field cancerization and/or non-melanoma skin cancer such as SCC, BCC and/or MCC.

Optionally, the subject has actinic keratoses, Bowenoid keratoses, Bowen's disease, skin field cancerization, and/or non-melanoma skin cancer such as SCC, BCC and/or MCC. Optionally, the subject has actinic keratoses (potentially among other conditions).

Optionally, the subject is a mammal. For example, the subject can be human. In some embodiments, the subject is Caucasian.

Further aspects of the present disclosure and further embodiments of the aspects described in the preceding paragraphs will become apparent from the following description, given by way of example and with reference to the accompanying drawings.

DETAILED DESCRIPTION OF THE EMBODIMENTS

It will be understood that the present disclosure as described and defined in this specification extends to all alternative combinations of two or more of the individual features mentioned or evident from the text or drawings. All of these different combinations constitute various alternative aspects of the disclosure.

Reference will now be made in detail to certain embodiments of the disclosure. While the disclosure will be described in conjunction with the embodiments, it will be understood that the intention is not to limit the disclosure to those embodiments. On the contrary, the disclosure is intended to cover all alternatives, modifications, and equivalents, which may be included within the scope of the present disclosure as defined by the claims.

Further aspects of the present disclosure and further embodiments of the aspects described in the preceding paragraphs will become apparent from the following description, given by way of example.

All of the patents and publications referred to herein are incorporated by reference in their entirety.

For purposes of interpreting this specification, terms used in the singular will also include the plural and vice versa.

The present disclosure relates to new methods for the treatment of clinical and pre-clinical skin damage, in particular, cancerous and precancerous skin. The method involves the use of a new tool for assessing cutaneous skin field cancerization to assess the severity of the skin damage and assist in the selection of a suitable treatment. The assessment of skin damage has historically been highly subjective and subject to significant inter-rater variation. While tools have been developed to assist with standardized assessment of individual skin lesions, suitable tools are yet to be developed for the standardized assessment of a skin field or a region of skin including multiple lesions and/or a base level of skin damage across all or part of the field. The skin field cancerization tool now developed allowed for an objective, standardized assessment of a skin field and has excellent reproducibility. Thereby addressing a key difficulty with the tools available in the art.

In addition, the present disclosure assists the selection of treatment for patients with clinical and pre-clinical skin damage. The scoring tool indicates when a more minor lesional therapy is appropriate, and when a more rigorous field therapy is indicated. Further, the tool indicates when the most effective and most invasive therapy, radiation therapy, is required. Radiation therapy on the skin is more recently developed than many of the therapies available. It is a powerful treatment but also invasive, requiring deliberately damaging the skin followed by controlled healing. The use of the tool will minimize the repeated ineffective use of lower efficacy treatments by increasing the likelihood that a subject that is in need of a stronger therapy is provided with one. In addition, the use of the tool will minimize the unnecessary use of invasive treatments, such as radiotherapy treatments, when they are not required.

As used herein, "skin field" is intended to refer to any anatomical region of skin. For example, head, scalp, forehead, nose, right cheek, left cheek, neck (optionally divided into the back of the neck and front of the neck), right forearm, left forearm, dorsum of the right hand, dorsum of the left hand, palm of the left hand, palm of the right hand, right lower leg, right upper leg, left upper leg, left lower leg, dorsum of the right foot, dorsum of the left foot, sole of the right foot, sole of the left foot, back (optionally the upper and lower back are considered separate fields), shoulders (optionally the right shoulder, left shoulder or across the top of the upper back), chest (optionally the upper chest and lower chest are considered separate fields), chest from the waist up, back from the waist up, abdomen, buttocks (optionally the right buttock and left buttock are considered separate fields), right upper arm, left upper arm, décolletage, right ear, left ear or combinations thereof including combinations of portions thereof, including the lower and upper left and/or right arm, the lower and upper left and/or right leg, the right cheek and right ear, the left cheek and left ear, the right cheek and right half of the forehead and optionally also the right ear and/or right half of the nose, the right half of the face, left cheek and left half of the forehead and optionally also the left ear and/or left half of the nose, and the left half of the face.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). For example, preventing the progress of actinic keratosis into (or into additional) skin cancers. Biological and physiological parameters for identifying such patients are provided herein and are also well known by clinicians.

As used herein, the terms "treatment" or "treating" of a subject includes delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The existence of, improvement in, treatment of or prevention of a condition described herein may be determined by any clinically or biochemically relevant method including analysis of a biopsy.

In the context of this disclosure a treatment of actinic keratosis/actinic keratoses will prevent the development of cancer, for example, squamous cell carcinoma and/or basal cell carcinoma.

As used herein, the term "subject in need thereof" is intended to refer to an individual who has clinical and/or subclinical skin damage including cancerous or pre-cancerous skin. Preferably, the "subject in need thereof" has actinic keratoses, Bowenoid keratoses, Bowen's disease, skin field cancerization, and/or non-melanoma skin cancer such as SCC, BCC and/or MCC.

As used herein, the terms "assessor" and "rater" are used interchangeably and are intended to mean the person or system that provides the skin field assessment scores (i), (ii), and/or (iii) used to calculate the SCFI.

As used herein, except where the context requires otherwise, the term "comprise" and variations of the term, such as "comprising", "comprises" and "comprised", are not intended to exclude further additives, components, integers or steps.

The methods of the present disclosure are particularly useful in the diagnosis and/or treatment of humans.

Inter-Rater Agreement

Inter-rater agreement is the propensity for two or more raters to independently classify a given patient into the same pre-defined category. Inter-rater agreement can be assessed statistically. For example, as demonstrated in Example 1.

Assessing Lesion Thickness

Dermatologists routinely assess lesion thickness. The assessment is completed visually and/or by touch, including, for example, by running a finger or thumb over the lesion.

This disclosure categorizes lesions as having: no thickness, thin thickness, moderate thickness, or very thick thickness. As used herein, "thin thickness" refers to just perceptible thickness. For example, thickness that is just observable visually or by touch. Thin thickness equates with lesions about 1 mm thick. As used herein, "moderate thickness" refers to easily felt or seen thickness. Moderate thickness excludes very thick lesions including cutaneous horns. Moderate thickness equates with lesions greater than 1 mm to about 3 mm thick. As used herein, "very thick thickness" refers to lesions with cutaneous horns. Very thick thickness equates with lesions greater than 3 mm thick.

These categories are similar to those used by the Olsen score, which has been used in practice by dermatologists for over 20 years.

The thickness categories in this disclosure are often written as:
 no thickness;
 thin thickness, just perceptible thickness, or about 1 mm thick;
 moderate thickness, easily felt or seen thickness, or greater than 1 mm to about 3 mm thick; and
 very thick, cutaneous horns, or greater than 3 mm thick.

In other words: thin thickness can be identified by assessing for "just perceptible thickness" or "about 1 mm thick". Moderate thickness can be identified by assessing for "easily felt or seen thickness" or "greater than 1 mm to about 3 mm thick". Very thick can be identified by assessing for "cutaneous horns" or "greater than 3 mm thick".

The Olsen Score

The Olsen score was developed by Doctor Olsen and published in 1991 in Olsen 1991. The test assesses the severity of a skin lesion as follows:

A lesion score of 1 to 3 was assigned to each patient on the basis of overall thickness of an actinic keratosis lesion:

1=mild or thin (slight palpability, with actinic keratoses felt better than seen), 2=moderate (moderately thick actinic keratoses that are easily seen and felt), 3=severe or very thick (very thick and/or obvious actinic keratoses).

Over the last 20 years this scoring system has been used widely to score the severity of individual lesions. In the examples of this specification a modified Olsen score was used as follows:

0=no thickness present

1=thin, slightly palpable or just perceptible (eg less than 1 mm)

2=moderate, easily felt or seen (eg greater than 1 to about 3 mm)

3=very thick, including cutaneous horns (eg greater than 3 mm)

Alternative Measures of Lesion Thickness

The thickness of a lesions, for example, the thickest lesion in the skin field can be measured directly. One method is to use scale bars placed on the skin next to the lesion and measure how far the lesion protrudes above the normal skin. Another method is to measure the stratum corneum hydration of an actinic keratosis lesion. This can be used to indirectly determine thickness of the lesion because hydration gradually decreases in keratotic tissue. Further information on this approach is included in Heerfordt (2016).

SCFI Scores

The calculation of the SCFI score is described in Example 1. The score ranges from 0-30. A skin field with a score of 0 is healthy and does not require treatment. A skin field with a score of 1-4 has more lesional than field treatment requirements. Generally, lesional treatments are suitable for skin fields with these scores such as freezing, for example, with liquid nitrogen, topical treatment with one of a variety of topical treatments currently available or physical removal by shaving or curetting. A skin field with a score of 5-14 has more field requirements than lesional requirements. However, the skin field has not advanced to a severity warranting the more aggressing treatments. Treatment will then usually still be freezing with liquid nitrogen, topical treatment with one of a variety of topical treatments currently available or physical removal by shaving or curetting or diathermy. However, more lesions will need treatment. If there are several cancerous skin lesions in the field, the treatment might be upgraded to one of the more invasive options. A skin field with a score of 15-30 is sufficiently severe to warrant field topical treatment or field radiation therapy.

Cancerous and Pre-Cancerous Skin

Actinic Keratosis

An actinic keratosis (also known as a solar keratosis) is a rough, scaly patch on skin that is often caused by years of exposure to the sun. Actinic keratoses are most commonly found on the face, lips, ears, back of your hands, forearms, lower legs scalp or neck.

An actinic keratosis enlarges slowly and usually causes no signs or symptoms other than a patch or small spot on your skin. These patches take years to develop, usually first appearing in people over 40.

A small percentage of actinic keratosis lesions can eventually become skin cancer.

The signs and symptoms of an actinic keratosis include:
rough, dry or scaly patch of skin, usually less than 1 inch (2.5 centimetres) in diameter flat to slightly raised patch or bump on the top layer of skin in some cases, a hard, wartlike surface color as varied as pink, red or brown itching or burning in the affected area Bowen's Disease Bowen's disease (also known as intra-epidermal squamous cell carcinoma or squamous cell carcinoma in situ) is a common superficial cancer of the skin. It appears most commonly as a slow-growing, persistent red scaly patch on areas of skin exposed to the sun. People with suppressed immune systems, either from medications or other medical problems, are at higher risk of Bowen's disease. Arsenic exposure can also lead to the development of Bowen's disease. Like actinic keratosis, if Bowen's disease is not treated, a small percentage may develop into an invasive skin cancer and/or squamous cell carcinoma (SCC).

Bowen's disease is defined clinically as a lesion showing 3 or more of the following features:

Size >5 mm

Shape irregular

Deep redness

Base induration

Hyperkeratosis/Cutaneous horn

Erosion/crusting

Squamous Cell Carcinoma

Squamous cell carcinoma (SCC) of the skin is the second most common form of skin cancer, characterized by abnormal, accelerated growth of squamous cells. When caught early, most SCCs are curable. In this specification, SCC refers to cutaneous SCC and not internal SCC.

The top layer of the skin (the epidermis) has three main types of cells. One layer is squamous cells. These are flat cells that shed continuously as new ones form. SCC occurs when DNA damage from exposure to ultraviolet radiation or other damaging agents trigger abnormal changes in the squamous cells.

SCCs can appear as scaly red patches, open sores, rough, thickened or wart-like skin, or raised growths with a central depression. At times, SCCs may crust over, itch or bleed. The lesions most commonly arise in sun-exposed areas of the body.

SCCs vary extensively in their appearance.

Basal Cell Carcinoma

Basal cell carcinoma (BCC) is a type of skin cancer. Basal cell carcinoma begins in the basal cells—a type of cell within the skin that produces new skin cells as old ones die off.

Basal cell carcinoma often appears as a slightly transparent bump on the skin, though it can take other forms. Basal cell carcinoma occurs most often on areas of the skin that are exposed to the sun, such as your head and neck.

Most basal cell carcinomas are thought to be caused by long-term exposure to ultraviolet (UV) radiation from sunlight. Avoiding the sun and using sunscreen may help protect against basal cell carcinoma.

Basal cell carcinoma appears as a change in the skin, such as a growth or a sore that will not heal. These changes in the skin (lesions) usually have one of the following characteristics:

A pearly white, skin-colored or pink bump that is translucent, meaning you can see a bit through the surface. Tiny blood vessels are often visible. In people with darker skin tones, the lesion may be darker but still somewhat translucent. The most common type of skin cancer is basal cell carcinoma. BCCs often appear on the face and ears. The lesion may rupture, bleed and scab over.

A brown, black or blue lesion—or a lesion with dark spots—with a slightly raised, translucent border.

A flat, scaly, reddish patch with a raised edge is more common on the back or chest. Over time, these patches can grow quite large.

A white, waxy, scar-like lesion without a clearly defined border, called morpheaform basal cell carcinoma, is the least common.

Topical Treatment Options

Cryotherapy, Cryosurgery or Liquid Nitrogen

The physician uses a cotton-tipped applicator or spray device to apply liquid nitrogen to freeze and destroy the tumor, which eventually falls off, allowing healthy skin to emerge.

Cryosurgery is effective for superficial SCCs, especially for patients with bleeding disorders, implantable cardiac devices or problems tolerating anaesthesia.

Laser Surgery

The physician directs a beam of intense light at the tumor to target the cancerous cells. Some lasers vaporize (ablate) the skin cancer, while others (nonablative lasers) convert the beam of light to heat, which destroys the tumor.

Laser surgery is not yet FDA-approved for SCC but is sometimes used for superficial SCCs, especially when other techniques have been unsuccessful.

Topical Chemotherapy 5-fluorouracil (5-FU), imiquimod, and ingenol mebutate are creams or gels that can be applied directly to affected areas of the skin to treat superficial SCCs with minimal risk of scarring. Imiquimod activates the immune system to attack cancerous cells, while 5-FU and ingenol mebutate are topical therapies that target cancerous and precancerous cells.

These medications are used to treat actinic keratoses, prevent further keratoses, and prevent progress of the keratoses to skin cancer. While these topical medications are not yet FDA-approved for treating SCCs, they are sometimes used to treat superficial tumors.

5-Fluorouracil 5-fluorouracil (Carac, Efudex, Fluoroplex, Tolak) (5-FU) cream or solution, a topical chemotherapy, is one of the most commonly used treatments for actinic keratoses, the most common skin precancers. It is especially effective for "field therapy," treating areas of skin with multiple lesions.

Efudex cream is also FDA-approved to treat superficial basal cell carcinoma, with cure rates between 80 and 90 percent, and is sometimes used for superficial squamous cell carcinoma. The 5-FU is rubbed gently onto and around the lesion once or twice daily for two to four weeks. Side effects include redness, swelling and crusting, but for many people, the therapeutic benefits outweigh any temporary discomfort. 5-FU can treat both visible and invisible lesions with a minimal risk of scarring. It is available in concentrations ranging from 0.5 to 5.0 percent.

Imiquimod

Imiquimod (Aldara, Zyclara) topical cream stimulates the immune system to produce interferon, a chemical that attacks cancerous and precancerous cells. It is especially effective for "field therapy," treating areas of skin with multiple lesions. Available in different strengths, it is usually applied two or three times a week for several weeks or months to treat people with multiple precancerous actinic keratoses. This immunotherapy is also FDA-approved to treat superficial basal cell carcinoma, rubbed gently into the tumor five times a week for six weeks or longer, with cure rates between 80 and 90 percent. It is used off-label (without FDA approval) for the treatment of some superficial squamous cell carcinomas. The most common side effects are flaking, itching, swelling, redness and other skin irritations, sometimes accompanied by diarrhoea, sinus infections and headaches. There is minimal risk of scarring.

Ingenol mebutate

Ingenol mebutate (Picato) gel, approved by the FDA in 2012, is the first topical therapy to treat precancerous actinic keratoses effectively with just two or three days of application time. It is available in one strength for the face and scalp and another for the rest of the body. Skin redness, flaking, scaling, crusting and swelling are the most common side effects. Ingenol mebutate can cause painful reactions in the first days of treatment, but these usually begin to improve within a week. There is minimal risk of scarring.

Curettage and Electrocautery

This technique can be used for both actinic keratoses (skin precancers) and certain skin cancers. Using local anaesthesia, the physician scrapes off part or all of the lesion with a curette, an instrument with a sharp ring-shaped tip. Then the doctor uses electrodessication, which cauterizes the area with heat or a chemical agent to stop the bleeding and destroy any residual abnormal cells that the curette did not remove. When treating a skin cancer, the doctor may repeat the entire procedure twice at the same session.

While curettage and electrodessication can be used to remove actinic keratoses as well as some superficial basal cell carcinomas (BCCs) and squamous cell carcinomas (SCCs), it is usually not recommended for larger, aggressive or invasive BCCs or SCCs or for lesions on the face. The treated area may not regain its pigment.

Photodynamic Therapy (PDT)

The physician applies a light-sensitizing topical agent and, after allowing a period of time for absorption, directs a strong blue or red light or laser at the tumor to activate the topical agent, killing cancer cells while sparing healthy tissue. After the procedure, patients must strictly avoid sunlight for at least 48 hours, as ultraviolet exposure will increase activation of the medication and may cause severe sunburns.

PDT can be used for some superficial SCCs on the face and scalp but is not recommended for invasive SCCs. It is most effective for treating actinic keratoses, which can be precursor lesions to SCC.

Surgery Including Mohs Micrographic Surgery

Using a scalpel, the physician removes, or excizes, the entire cancerous tumor along with a surrounding border of presumably normal skin as a safety margin, then sends the tissue specimen to a lab to make sure the margins are free of cancer. Depending on its size and location, the wound may be left open to heal or the doctor may close it with stitches. If the lab finds evidence of skin cancer beyond the safety margin, the patient may need to return for another surgery.

Excisional surgery can be used for basal cell carcinomas (BCCs) and squamous cell carcinomas (SCCs) as well as melanomas. For tumors discovered at an early stage that have not spread beyond the tumor margin, excisional surgery is frequently the only treatment required.

Mohs surgery has long been the gold standard for treating many BCCs and SCCs. It is especially beneficial in areas of the face where preserving normal tissue is essential for function and appearance. It is also used for BCCs and SCCs that have recurred following standard treatment. Mohs surgery can pinpoint and remove microscopic extensions, or "roots," of the cancer, and because SCCs have a higher risk of spreading (metastasizing) than BCCs, complete microscopic removal is extremely important.

The Mohs procedure is done in stages, with each removed layer of tissue examined under a microscope in an on-site lab at the time of surgery, while the patient waits. This is different from standard excision, in which the physician closes the wound after removing the tumor, allows the patient to go home and sends the excized tissue to a lab for a pathologist to review.

After injecting a local anaesthetic, the Mohs surgeon first removes the visible cancerous tumor and a very small margin of presumably healthy tissue. After the wound is bandaged, the patient waits.

The surgeon color-codes the excized tissue and draws a map that correlates the tissue with the surgical site on the face or body of the patient. Next, a technician processes the tissue in an on-site laboratory by freezing the tissue, slicing it horizontally and placing the slices on slides. These "sections," encompassing the margins of the tissue, are stained with special chemicals that help identify cancerous tissue. The Mohs surgeon then examines these sections under a microscope. If the doctor finds any remaining cancer cells, he or she pinpoints the areas on the map, and calls the patient back into the operating room. The Mohs surgeon then removes more tissue exactly where cancer cells remain.

The team repeats this process until the surgical site contains no microscopic evidence of cancer. If more than one or two rounds are needed, the entire process can take up to several hours. Depending on its size and location, the wound may be left open to heal or the surgeon may close it with stitches. In some cases, a wound may need reconstruction using neighboring tissue or a skin graft. In some cases, a plastic surgeon may perform the reconstruction.

This precise technique has the highest cure rate and lowest recurrence rate of any skin cancer treatment, while preserving the maximum amount of normal tissue and allowing the smallest scar possible.

Long considered the single most effective technique for removing BCCs and SCCs, Mohs surgery had not been widely used for melanomas until recently, as this type of cancer was hard to distinguish on frozen sections. But advances in the field are changing that, and a growing body of evidence suggests that the Mohs procedure is safe and effective for both in situ and invasive melanoma. The use of Mohs surgery for any type of skin cancer requires special training.

Radiotherapy (Radiation Therapy)

The physician uses low-energy X-ray beams to destroy the tumor, with no need for cutting or anesthesia. Destruction of the tumor may require several treatments over a few weeks or daily treatments for a specified time.

Radiation therapy is primarily used for SCCs that are hard to treat surgically, and in elderly patients or people in poor health for whom surgery is not advised. For some cases of advanced SCC, especially those with perineural involvement, radiation may be used after surgery, or in combination with other treatments.

Chemical Peel

To repair superficial skin damage, the physician applies trichloroacetic acid and/or similar chemicals to the face, causing the top skin layers to slough off. New skin generally regrows within a few weeks. This method may require local anaesthesia. It can cause temporary irritation and discoloration.

A chemical peel can be used to remove superficial facial actinic keratoses (precancerous skin lesions), especially when previous treatments have not succeeded. It is also used as a cosmetic skin rejuvenation technique.

REFERENCES

Glogau R G. The risk of progression to invasive disease. Journal of the American Academy of Dermatology. 2000; 42(1):S23-S4 (Glogau 2000).

Gwet, K. L., *Computing inter-rater reliability and its variance in the presence of high agreement*. Br J Math Stat Psychol, 2008.61(Pt 1): p. 29-48 (Gwet 2008).

Gwet, K. L., *Handbook of Inter-Rater Reliability: The Definitive Guide to Measuring the Extent of Agreement Among Raters*. 4th Edition. 2014, Gaithersburg, Md.: Advanced Analytics (Gwet 2014).

Heerfordt, I. M, *Thickness of actinic keratosis does not predict dysplasia severity or P53 expression*. Sci Rep, 2016, 6:33952 (Heerfordt 2016).

Landis, J. R. and G. G. Koch, *The measurement of observer agreement for categorical data. Biometrics*, 1977.33(1): p. 159-74. (Landis 1977).

Olsen E A, Lisa Abernethy M, Kulp-Shorten C, Callen J P, Glazer S D, Huntley A, et al. A double-blind, vehicle-controlled study evaluating masoprocol cream in the treatment of actinic keratoses on the head and neck. Journal of the American Academy of Dermatology. 1991; 24(5):738-43 (Olsen 1991).

EXAMPLES

Example 1

Inter-Rater Agreeability of the Skin Field Cancerization Tool (SFCT)

This study assesses the inter-rater agreement of the SFCT across two rounds of photographic validation with 60 cases, by seven expert dermatologists.

Materials and Methods

Development of the Skin Field Cancerization Tool:

Seven board-certified expert dermatologists from around Australia (QLD (n=2), VIC (n=2), NSW (n=1) WA (n=1) and SA (n=1)) met to assess two versions of the Skin Field Cancerization Index (SFCI).

Both versions included assessment of the number of actinic keratoses in the field, thickness of actinic keratoses in the field and area of involvement in the field. In addition, the first version of the SFCI included assessment of 'atypical keratosis'—keratoses that show signs of inflammation, larger lesions or clinically appear to be skin cancers such as SCC or BCC. Following validation round 1, the assessment of atypical keratosis was found to be a key factor in reduced agreement between individual scorers. This atypical keratosis assessment was replaced with a score for 'cancer evident in zone' in the second version of the SFCI.

In addition, a global assessment score was assessed.

Score Design

The SFCT is a composite index score which assesses field cancerization at a specific skin field. The score measures individual regions of skin field characterization and is designed to independently measure these areas for assessment for treatment purposes.

The second version of the SFCT is made up of three components: the skin field cancerization index (SFCI) which assesses area of skin involved and actinic keratosis, the global assessment score and cancer-in-zone score.

proven histologically within the past 6 months. A score of '+' indicates that cancer is present or has occurred in the zone. A score of '−' indicates that no cancer is present or has occurred in the zone.

TABLE 1

Skin Field Cancerization Tool, Version 2

| Clinical feature Score | Number of actinic keratoses 0-3 | Thickness of keratoses (based on thickest keratoses present) 0-3 | Area of involvement 0-5 | Global assessment score 0-4 | Cancer evident in zone + or − |
|---|---|---|---|---|---|
| Criteria | 0: no sign of keratosis 1: mild signs of keratoses: Few ie 5 or less discrete lesions 2: moderate signs of keratoses: Greater than 5 discrete lesions 3: severe keratoses: keratoses are continuous (ie no longer individually distinct) or extensive lesion numbers (ie over 15) | 0: no thickness present 1: thin, slightly palpable or just perceptible (eg about 1 mm) 2: moderate, easily felt or seen (about >1 to 3 mm) 3: very thick, including cutaneous horns (>3 mm or more) This assessment is an application of the Olsen score | 0: no area of involvement 1: small area of involvement (1-5%) 2: less than ⅓ of the area is involved 3: ⅓-⅔ of the area is involved 4: >⅔ of the area is involved 5: almost all - all of the area is involved (96-100%) | 0: skin in the zone is generally smooth with no keratosis evident 1: mild - small area in the field affected with few or thin keratoses 2: moderate - patchy involvement in the zone with moderately thick keratoses 3: severe - extensive involvement of the zone with numerous thicker keratoses 4: very severe - extensive involvement of the zone with numerous thicker keratosis with cutaneous horn and/or confluent (ie continuous) keratoses | +: cancer present or has occurred in zone in the past six months −: NO cancer present or has occurred in zone in the past six months |

SFCI Score = (number of actinic keratoses + thickness of keratoses) × area of involvement The algorithm for calculating the SFCI is: (NK+TK)×A where: NK is Number of Actinic Keratoses, TK is Thickness of Keratoses and A is the clinical Area of involvement in the field. This calculation yields a result between 0 to 30 (0 being completely clear, 30 being extremely severe). Severity of NK is scored on a four-point scale (nil=0, mild=1, moderate=2 and severe=3) and TK is scored on a four-point scale (nil=0, thin=1, moderate=2 and very thick=3). A is scored on a 5-point scale and is a measure of the investigator's perceived area of defined zone (ie skin field) involvement (nil=0, 1-5% =1, less than ⅓=2, ⅓-⅔=3, greater than ⅔ of the area to 95%=4, 96-100%=5). Alternatively, A is scored as nil=0, 1-5%=1, 6 to 32%=2, 33 to 67%=3, 68 to 95%=4, 96-100%=5.

In addition to the SFCI, a global assessment score was performed as an overall assessment of the field or the zone. This is scored on a five-point scale which ranges from non-affected skin to mild, moderate, severe and very severe field cancerization.

Furthermore, an assessment of cancer in the assessed zone is the final component of the SFCT. This assessment can be based on clinical diagnosis at the time of the assessment or Photographic Validation of the SFCT De-identified photographs of 60 patients aged 18+ with varying degrees of skin field cancerization affecting a range of anatomical sites (e.g. head, forearm, dorsum of hand, lower leg) were assessed. Photographs were excluded if other dermatoses present in the images may have confounded assessment.

The photographic validation of the SFCT occurred over two rounds. The Delphi scoring method was selected for its ability to obtain reliable consensus from an expert panel.

Thirty photographic cases were assessed in each round of validation. The protocol for scoring was as follows, in accordance with the Delphi method:

1. Panel members individually scored the photograph
2. The scores were handed in to the researcher de-identified
3. The results of the scores were revealed to the group
4. A group discussion with the panel took place regarding the group's scores
5. There was then an opportunity for individuals to revise their score Statistical Methods Statistical analyses were completed using Stata. Inter-rater agreement is defined as the propensity for two or more raters to independently classify a given patient into the same pre-defined category. Inter-rater agreement was assessed using Kappa, implemented as kappaetc in Stata. This procedure allows a weighting where three or more raters have been used. Kappa was calculated according to the method of Gwet 2008 & Gwet 2014. This method does not assume independence between raters. Ordinal weights were applied to ordinal measures, and quadratic weights were applied to the skin field cancerization score.

The estimated coefficients are reported with their standard errors, and includes the smallest cumulative membership probability for each coefficient to fall into the selected benchmark interval. Standard errors are two-sided. The extent of agreement was considered poor if the coefficient was <0.00; slight if 0.00 to 0.20; fair if 0.21 to 0.40; moderate if 0.41 to 0.60; substantial if 0.61 to 0.80; and almost perfect if 0.81 to 1.00 (Landis 1977).

Correlations were conducted between the SFCI and the global score.

Results

Inter-Rater Reliability of the Skin Field Cancerization Tool

In the first round of photographic validation, the majority of components of the SFCT achieved at least 'substantial' inter-rater agreement. These were: area score, keratosis thickness, SFCI and the global score. The 'keratosis number' component of the SFCI achieved 'almost perfect' inter-rater agreement. The worst performing inter-rater agreement was with atypical keratosis (Gwet's AC 0.53 SE 0.07). Atypical keratosis was removed from the SFCI calculation to determine whether this changed the level of inter-rater agreement for the SFCI. There was no difference in agreement using the alternative scoring method, with both calculation methods achieving 'substantial' agreement. The results of the inter-rater agreement analysis are reported in Table 2.

For validation round 2, the inter-rater agreement in "cancer evident in zone" score was fair (Gwet's AC 0.33 SE 0.09). All other measures had almost perfect inter-rater agreement (Gwet's AC coefficient >0.80). The global score was significantly positively correlated to the skin field cancerization score (correlation coefficient 0.87, p<0.0001). The results of the inter-rater agreement analysis are reported in Table 2.

The results of the inter-rater agreement analysis for validation round 2 are reported in Table 3. For validation round 2, the inter-rater agreement in cancer score was fair (Gwet's AC 0.33 SE 0.09). All other measures had almost perfect inter-rater agreement (Gwet's AC coefficient >0.80). The global score was significantly positively correlated to the skin field cancerization score (correlation coefficient 0.87, p<0.0001).

TABLE 3

Summary of inter-rater agreement for validation round 2

| Rater | Keratosis Number | Keratosis Thickness | Area Score | Skin Field Cancerization | Global Score | Cancer Score |
|---|---|---|---|---|---|---|
| Dermatologist | Almost perfect | Almost perfect | Almost perfect | Almost perfect | Almost perfect | Fair |

Note:
summary ratings are based on the returned coefficient, not the probabilistic benchmark Agreement Between SFCI and Global Score of Field Cancerization In validation round 1, the global score was significantly positively correlated to the SFCI (correlation coefficient 0.82, p<0.0001). In validation round 2, the global score was significantly positively correlated to the SFCI (correlation coefficient 0.87, p<0.0001).

Discussion

This validation study demonstrates that the novel SFCT objectively assesses skin field cancerization at multiple anatomical sites with excellent inter-rater reliability among expert dermatologists. So far as the inventors are aware, the SFCT is the first tool to assess skin field cancerization specifically.

The SFCT's inter-rater agreement improved from 'substantial' across the majority of components for round 1, except atypical keratosis (moderate agreement), to excellent in round 2 for all components, except the 'cancer-in-zone', which achieved 'air' reproducibility. In addition, the global score, a component of the SFCT, was significantly positively correlated with the SFCI across both rounds of validation (correlation coefficient 0.82, p<0.0001 for round 1 and correlation coefficient 0.87, p<0.0001 for round 2).

The SFCT incorporates a global assessment score that acts as another, more holistic assessment of disease severity.

TABLE 2 inter-rater agreement for SFCI for photographic validation round 1 and 2. Reported as Kappa values (standard error)

| Validation round | Keratosis number | Keratosis thickness | Area score | Atypical keratosis/cancer in zone | Skin field cancerization Index | Skin field cancerization index (alternate) | Global score |
|---|---|---|---|---|---|---|---|
| 1 | 0.85 (0.02) | 0.76 (0.04) | 0.64 (0.04) | 0.53 (0.07) | 0.63 (0.04) | 0.7 (0.03) | 0.69 (0.04) |
| 2 | 0.91 (0.01) | 0.89 (0.02) | 0.86 (0.03) | 0.33 (0.09) | 0.81 (0.03) | n/a | 0.85 (0.02) |

Note:
Atypical keratosis was included in the SFCI for validation round 1 whereas this was replaced with cancer-in-zone for validation round 2. Skin field cancerization (alternate) refers to the SFCI calculation when atypical keratosis was removed from this calculation.

Summary

In the first round of validation, the SFCT achieved 'substantial' inter-rater agreement across all components of the tool except atypical keratosis (moderate agreement) and keratosis number (excellent agreement).

In the second round of validation, the SFCT achieved 'excellent' inter-rater agreement across all components, except 'cancer-in-zone', which achieved 'fair' reproducibility.

In addition, the global score, a component of the SFCT, was significantly positively correlated with the SFCI across both rounds of validation (correlation coefficient 0.82, $p<0.0001$ for round one and correlation coefficient 0.87, $p<0.0001$ for round two).

Example 2

Correlating Scores and Treatment

Photographs of photo damaged skin from multiple individuals and multiple skin fields were taken and scored in accordance with the skin field cancerization tool as described in Example 1. The scorer (a dermatologist) also developed a treatment plan based on their assessment of the skin damage. The results are shown in table 4 below.

TABLE 4

Results of recommended treatment based on Scores

| | | SFCI SCORE | | | | GLOBAL SCORE | CANCER SCORE | |
|---|---|---|---|---|---|---|---|---|
| | SITE | Keratosis Number 0 to 3 | Keratosis Thickness 0 to 3 | Area Score 0 to 5 | Total Score 0 to 30 | Global Score 0 to 4 | Cancer Evident + or − | Dermatologist recommended treatment |
| 1 | nose | 3 | 1 | 4 | 16 | 2 | positive | Topical 5-fluorouracil/imiquimod to field |
| 2 | forehead bilateral | 1 | 2 | 2 | 6 | 2 | positive | 1. Radiotherapy of cancer or surgery of the cancer & 2. Cryotherapy or lesional 5-fluorouracil/imiquimod to keratoses |
| 3 | forehead right | 3 | 2 | 4 | 20 | 3 | positive | 1. Radiotherapy of cancer & radiotherapy to the field; or 2. Surgery of cancer & topical 5-fluorouracil to field |
| 4 | nose | 3 | 1 | 3 | 12 | 2 | negative | Topical 5-fluorouracil/imiquimod to field |
| 5 | hand left | 3 | 2 | 4 | 20 | 3 | negative | Topical 5-fluorouracil or radiotherapy to the field |
| 6 | scalp | 3 | 3 | 4 | 24 | 4 | positive | Radiotherapy to the field |
| 7 | lower leg right | 2 | 2 | 3 | 12 | 2 | negative | Topical 5-fluorouracil to the field |
| 8 | scalp | 3 | 3 | 4 | 24 | 4 | positive | 1. Skin cancer radiotherapy or surgery & 2. Radiotherapy to the field |
| 9 | scalp | 3 | 2 | 5 | 25 | 3 | negative | Radiotherapy to the field or field topical 5-fluorouracil |
| 10 | cheek left | 3 | 1 | 4 | 16 | 3 | negative | Field topical 5-fluorouracil |
| 11 | ear left | 1 | 1 | 2 | 4 | 1 | negative | Cryotherapy or topical 5-fluorouracil/imiquimod to the lesion(s) |
| 12 | forehead | 3 | 1 | 3 | 12 | 2 | negative | Topical 5-fluorouracil/imiquimod to the field |
| 13 | hand right | 3 | 2 | 4 | 20 | 3 | negative | Radiotherapy to the field or topical 5-fluorouracil/imiquimod to the field |
| 14 | hand left | 1 | 2 | 3 | 9 | 2 | positive | 1. Surgery or radiotherapy of cancer & 2. Cryotherapy or lesional 5-fluorouracil/imiquimod to keratosis |
| 15 | back | 3 | 3 | 5 | 30 | 4 | positive | Radiotherapy to the field |
| 16 | scalp | 1 | 2 | 2 | 6 | 2 | negative | Cryotherapy |
| 17 | scalp | 3 | 3 | 5 | 30 | 4 | positive | Radiotherapy of cancer & radiotherapy to the field |
| 18 | nose | 1 | 1 | 1 | 2 | 1 | positive | Topical 5-fluorouracil to the lesion(s) |
| 19 | ear | 3 | 2 | 4 | 20 | 3 | negative | Topical 5-fluorouracil to the field |
| 20 | dorsum hand | 3 | 3 | 5 | 30 | 4 | positive | Radiotherapy of cancer & radiotherapy to the field |
| 21 | forearm | 2 | 2 | 3 | 12 | 2 | negative | Topical imiquimod to field |
| 22 | Right cheek | 2 | 1 | 2 | 6 | 1 | negative | Topical 5-fluorouracil to the lesion(s) |
| 23 | Right hand | 2 | 2 | 2 | 8 | 2 | negative | Cryotherapy |
| 24 | nose | 3 | 2 | 3 | 15 | 3 | positive | Topical 5-FU to the field |
| 25 | Scalp | 3 | 3 | 5 | 30 | 4 | positive | Radiotherapy to the field |
| 26 | Right hand | 2 | 2 | 2 | 8 | 1 | negative | Cryotherapy |

TABLE 4-continued

Results of recommended treatment based on Scores

| | SITE | SFCI SCORE | | | | GLOBAL SCORE | CANCER SCORE | Dermatologist recommended treatment |
|---|---|---|---|---|---|---|---|---|
| | | Keratosis Number 0 to 3 | Keratosis Thickness 0 to 3 | Area Score 0 to 5 | Total Score 0 to 30 | Global Score 0 to 4 | Cancer Evident + or − | |
| 27 | Right hand | 3 | 3 | 4 | 24 | 3 | negative | VMAT |
| 28 | Left forearm | 3 | 2 | 3 | 15 | 2 | negative | Topical 5-fluorouracil/imiquimod to field |

Correlation between SCFI and treatment:

| SCFI score | Appropriate treatment |
|---|---|
| 1 to 9 | Lesional therapy |
| 10 to 30 | Field therapy |

More specific correlation between SCFI and treatment:

| SCFI score | Appropriate treatment |
|---|---|
| 1 to 9 | Lesional therapy |
| 10 to 19 | Initial treatment topical field therapy (in the event of treatment failure secondary treatment with field radiotherapy recommended) |
| 20 to 30 | Either topical field therapy or field radiotherapy |

Even more specific correlation between SCFI and treatment:

| SCFI score | Appropriate treatment |
|---|---|
| 1 to 9 | Lesional therapy |
| 10 to 19 | Initial treatment topical field therapy (in the event of treatment failure secondary treatment with field radiotherapy recommended) |
| 20 to 25 | Either topical field therapy or field radiotherapy |
| 24 or 25 with a keratosis thickness score of 3 | Field radiotherapy |
| 26 or more | Field radiotherapy |

Correlation between Global Score and treatment:

| Global score | Appropriate treatment |
|---|---|
| Global score of 4 | Field radiotherapy |
| Global score of 3 | Either topical field therapy or field radiotherapy |
| Global score of 2 | Lesional therapy or a topical field therapy |
| Global score of 1 | Lesional therapy |

Where there is cancer in the field, surgery or radiation of the cancer may be recommended in addition to the field or lesional therapy. Alternatively, the field or lesional therapy may be sufficient. This depends on the severity of the cancer rather than the severity of the field damage as a whole.

Statements of Select Disclosure Embodiments

Statement 1. A method for assessing the severity of clinical or pre-clinical skin damage in at least one skin field in a subject comprising
(i) assessing the number of keratoses in the skin field;
(ii) assessing the thickness of the thickest keratosis in the skin field;
(iii) assessing the proportion of the field affected by clinical or subclinical skin damage; and
assigning the skin field with a severity score based on the assessments made in (i), (ii) and (iii).

Statement 2. A method for assessing the severity of clinical or pre-clinical skin damage in at least one skin field in a subject comprising
(i) assessing the number of keratoses in the skin field and assigning the skin field with a score based on the result of the assessment;
(ii) assessing the thickness of the thickest keratosis in the skin field and assigning the skin field with a score based on the result of the assessment;
(iii) assessing the proportion of the field affected by clinical or subclinical skin damage and assigning the skin field with a score based on the result of the assessment; and
assigning the skin field with a severity score based on the scores assigned in (i), (ii) and (iii).

Statement 3. A method for classifying a subject for eligibility for skin field therapy comprising
(i) assessing the number of keratoses in the skin field and assigning the skin field with a score based on the result of the assessment;
(ii) assessing the thickness of the thickest keratosis in the skin field and assigning the skin field with a score based on the result of the assessment;
(iii) assessing the proportion of the field affected by clinical or subclinical skin damage and assigning the skin field with a score based on the result of the assessment; and
assigning the skin field with a severity score based on the scores assigned in (i), (ii) and (iii).

Statement 4. A non-invasive method for collecting data useful for determining severity of clinical or pre-clinical skin damage in at least one skin field in a subject, the method comprising:
(i) assessing the number of keratoses in the skin field and assigning the skin field with a score based on the result of the assessment;
(ii) assessing the thickness of the thickest keratosis in the skin field and assigning the skin field with a score based on the result of the assessment; and (iii) assessing the proportion of the field affected by clinical or subclinical skin damage and assigning the skin field with a score based on the result of the assessment.

Statement 5. A non-invasive method for collecting data useful for classifying a subject for eligibility for skin field therapy, the method comprising:
  (i) assessing the number of keratoses in the skin field and assigning the skin field with a score based on the result of the assessment;
  (ii) assessing the thickness of the thickest keratosis in the skin field and assigning the skin field with a score based on the result of the assessment; and
  (iii) assessing the proportion of the field affected by clinical or subclinical skin damage and assigning the skin field with a score based on the result of the assessment.

Statement 6. A method of treating clinical or pre-clinical skin damage in a subject in need thereof comprising selecting at least one skin field
  (i) assessing the number of keratoses in the skin field and assigning the skin field with a score based on the result of the assessment;
  (ii) assessing the thickness of the thickest keratosis in the skin field and assigning the skin field with a score based on the result of the assessment;
  (iii) assessing the proportion of the field affected by clinical or subclinical skin damage and assigning the skin field with a score based on the result of the assessment; and
    based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy.

Statement 7. A method for monitoring the response of a subject o treatment for clinical or pre-clinical skin damage, the method comprising
  (i) assessing the number of keratoses in the skin field and assigning the skin field with a score based on the result of the assessment;
  (ii) assessing the thickness of the thickest keratosis in the skin field and assigning the skin field with a score based on the result of the assessment;
  (iii) assessing the proportion of the field affected by clinical or subclinical skin damage and assigning the skin field with a score based on the result of the assessment; and
  based on the scores assigned in (i), (ii) and (iii) treating the subject by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy, and
    following treatment repeating assessments (i), (ii) and (iii) and comparing the initial and repeated assessments to monitor the subject's response to the treatment.

Statement 8. A method for monitoring the response of a subject to treatment for clinical or pre-clinical skin damage, the method comprising
  a) prior to the subject receiving treatment
    (i) assessing the number of keratoses in the skin field and assigning the skin field with a score based on the result of the assessment;
    (ii) assessing the thickness of the thickest keratosis in the skin field and assigning the skin field with a score based on the result of the assessment;
    (iii) assessing the proportion of the field affected by clinical or subclinical skin damage and assigning the skin field with a score based on the result of the assessment; and
  b) after the subject receiving treatment repeating assessments (i), (ii) and (iii);
  and comparing the assessments of a) and b) to monitor the subject's response to the treatment.

Statement 9. The method of statement 8, wherein a decrease in any one or more of the scores for (i), (ii) and (iii) obtained in b) as compared to any one or more of the scores of i), (ii) and (iii) obtained in a) is indicative of the subject responding to the treatment, and/or is indicative of improvement resulting from the treatment in the clinical and/or pre-clinical skin damage.

Statement 10. The method of any one of statements 4 to 9, wherein a severity score is assigned to the skin field based on the scores assigned in (i), (ii) and (iii) and optionally, the severity score cannot be zero or the severity score is at least 1.

Statement 11. The method of any one of statements 1-9, wherein assessment (i) involves assessing the skin field as including mild, moderate, or severe keratoses.

Statement 12. The method of statement 11, wherein a score of 1-3 is allocated for the skin field assessed in assessment (i) for mild, moderate, or severe keratoses, respectively.

Statement 13. The method of statement 11 or statement 12, wherein the skin field is assessed as mild in assessment (i) because there are 5 or fewer (for example 1 to 5) discrete lesions in the skin field.

Statement 14. The method of any one of statements 11 to 13, wherein the skin field is assessed as moderate in assessment (i) because there are more than 5 discrete lesions in the skin field and no continuous keratoses.

Statement 15. The method of statement 14, wherein the skin field is assessed as moderate in assessment (i) further because there are 15 or fewer lesions (for example, 6 to 15 lesions) in the skin field.

Statement 16. The method of any one of statements 11-15, wherein the skin field is assessed as severe in assessment (i) because the subject's keratosis is continuous and/or there are more than 15 discrete lesions in the skin field.

Statement 17. The method of any one of statements 11-16, wherein a score of 1-3 is allocated for the skin field assessed in assessment (i) as follows:
  1 for 5 or fewer (for example 1 to 5) discrete lesions in the skin field and no continuous keratoses;
  2 for more than 5 discrete lesions in the skin field and no continuous keratoses; and
  3 for continuous keratosis and/or more than 15 discrete lesions in the skin field.

Statement 18. The method of statement 17, wherein the score of 2 is further allocated because there are 15 or fewer lesions (for example, 6 to 15 lesions) in the skin field.

Statement 19. The method of any one of statements 1-18, wherein assessment (ii) involves assessing the thickest keratoses in the skin field in accordance with the Olsen score, a modified Olsen score, direct measurement of the thickness of the keratosis and/or indirect measurement of thickness of the actinic keratosis by measurement of the stratum corneum hydration of the actinic keratosis.

Statement 20. The method of any one of statements 1-19, wherein assessment (ii) involves assessing the thickest keratoses in the skin field as having no thickness, having thin thickness (ie just perceptible thickness), having moderate thickness (ie easily felt or seen thickness), or being very thick including having cutaneous horns.

Statement 21. The method of any one of statements 1-19, wherein assessment (ii) involves assessing the thickest keratoses in the skin field as having no thickness, being about 1 mm thick, being greater than 1 to about 3 mm thick, being more than 3 mm thick.

Statement 22. The method of statement 20 or statement 21, wherein a score of 0-3 is allocated for the skin field assessed in assessment (ii) as follows:
0 for no thickness;
1 for thin thickness;
2 for moderate thickness; and
3 for very thick, wherein
(i) thin thickness is just perceptible thickness, moderate thickness is easily felt or seen thickness, and very thick is cutaneous horns; or
(ii) thin thickness is about 1 mm thick, moderate thickness is greater than 1 mm to about 3 mm thick, and very thick is greater than 3 mm thick.

Statement 23. The method of any one of statements 1-22, wherein assessment (iii) involves assessing whether no area, 1-5% of the area, less than ⅓ of the area (or 6-33% of the area), ⅓-⅔ of the area (or 34-66% of the area), greater than ⅔ of the area to 95% of the area (or 67-95% of the area), or 96-100% of the area in the skin field is affected by clinical and/or pre-clinical skin damage.

Statement 24. The method of statement 23, wherein a score of 0-5 is allocated for the skin field assessed in assessment (iii) as follows
0 for no area affected;
1 for 1-5% of the area affected;
2 for less than ⅓ of the area affected (or 6-33% of the area);
3 for ⅓-⅔ of the area affected (or 34-66% of the area);
4 for greater than ⅔ of the area to 95% of the area affected (or 67-95% of the area), or
5 for 96-100% of the area in the skin field affected.

Statement 25. The method of statement 24, wherein the score for assessment (i) is added to the score for assessment (ii) and the sum of those scores is multiplied by the score for assessment (iii) to determine a final skin cancerization field index (SCFI) score for the skin field.

Statement 26. The method of statement 25, wherein the skin field has an SCFI score of 15 or greater and is treated with a skin field therapy.

Statement 27. The method of statement 25, wherein the skin field has an SCFI score of 10 or greater and is treated with a skin field therapy.

Statement 28. The method of statement 25, wherein, when the skin field has an SCFI score of 10 or greater, the skin field is treated with a skin field therapy and, when the skin field has an SCFI score of 1 to 9, the skin field is treated with a lesional therapy.

Statement 29. The method of any one of statements 26 to 28, wherein the skin field therapy is radiation therapy or the field application of a topical treatment.

Statement 30. The method of statement 25, wherein the skin field has an SCFI of 10 to 19 and is treated with the field application of a topical treatment.

Statement 31. The method of statement 25, wherein the skin field has an SCFI of 20 to 30 and is treated with either field radiation therapy or the field application of a topical treatment.

Statement 32. The method of statement 25, wherein
(i) when the skin field has an SCFI score of 20 to 30, the skin field is treated with field radiotherapy or the field application of a topical treatment;
(ii) when the skin field has an SCFI of 10 to 19, the skin field is treated with the field application of a topical treatment; and
(iii) when the skin field has an SCFI score of 1 to 9, the skin field is treated with a lesional therapy.

Statement 33. The method of statement 25, wherein the skin field has an SCFI of 20 to 25 and is treated with either field radiation therapy or the field application of a topical treatment.

Statement 34. The method of statement 25, wherein the skin field has an SCFI of 26 to 30 and is treated with field radiation therapy.

Statement 35. The method of statement 25, wherein
(i) when the skin field has an SCFI score of 26 to 30, the skin field is treated with field radiotherapy;
(ii) when the skin field has an SCFI score of 20 to 25, the skin field is treated with field radiotherapy or the field application of a topical treatment;
(iii) when the skin field has an SCFI score of 10 to 19, the skin field is treated with the field application of a topical treatment; and
(iv) when the skin field has an SCFI score of 1 to 9, the skin field is treated with a lesional therapy.

Statement 36. The method of statement 25, wherein the subject has an SCFI of 24 or 25 and a 3 for the score of assessment (ii) and is treated with field radiation therapy.

Statement 37. The method of statement 25, wherein
(i) when the skin field has an SCFI score of 26 to 30, the skin field is treated with field radiotherapy;
(ii) when the skin field has an SCFI score of 24 or 25 and a 3 for the score of assessment (ii), the skin field is treated with field radiotherapy;
(iii) when the skin field has an SCFI score of 20 to 25 but not a score of 24 or 25 with a 3 for the score of assessment (ii), the skin field is treated with field radiotherapy or the field application of a topical treatment;
(iv) when the skin field has an SCFI of 10 to 19, the skin field is treated with the field application of a topical treatment; and
(v) when the skin field has an SCFI score of 1 to 9, the skin field is treated with a lesional therapy.

Statement 38. The method of any one of statements 29 and 31 to 37, wherein the topical treatment does not adequately treat the skin field and the patient is subsequently treated with field radiation therapy.

Statement 39. The method of any one of statements 29 and 31 to 38, wherein the radiation therapy includes one or more lesional tumorcidal radiation therapy boosts to treat one or more specific lesion.

Statement 40. The method of statement 29, wherein the skin field includes 1 or 2 simultaneous cancerous lesions and the patient is treated with radiation therapy including one or more lesional tumorcidal radiation therapy boosts to treat the cancerous lesions, or surgical removal of the cancerous lesions followed by field radiation therapy.

Statement 41. The method of statement 25, wherein the skin field has an SCFI of 1-9 and is treated with a lesional therapy.

Statement 42. The method of any one of statements 28, 32, 35, 37, and 41, wherein the lesional therapy is (a) freezing one or more lesions with liquid nitrogen, (b) shaving, curetting or surgically removing one or more lesions, or (c) applying a topical treatment to one or more lesions.

Statement 43. The method of any one of statements 29 to 33, 35, 37 and 38, wherein the topical treatment is 5-fluorouracil, imiquimod, ingenol mebutate, diclofenac or photodynamic therapy.

Statement 44. The method of any one of statements 26 to 43, wherein the treatment results in an 80% or more improvement in the SCFI score and/or an SCFI score of less than 5.

Statement 45. The method of any one of statements 1 to 44, wherein assessments (i), (ii) and (iii) are each made independently by an assessor with reference to one or more of a visual assessment of the skin field, dermoscopic analysis of the skin field, analysis of one or more images of the skin field, reference to one or more biopsy results for one or more of the lesions in the skin field, and/or reference to the subject's medical history.

Statement 46. The method of any one of statements 1 to 45, wherein the assessment of (i), (ii) and (iii) is performed on one or more image of the skin field.

Statement 47. The method of statement 45 or 46, wherein the assessment is of one or more images of the skin and the images are physical and/or electronic.

Statement 48. The method of statement 46 or 47, wherein the one or more images of the skin field are obtained prior to assessments (i), (ii) and (iii).

Statement 49. The method of any one of statements 46 to 49, wherein the images are photographs, video and/or scans.

Statement 50. The method of any one of statements 1 to 49, wherein assessments (i), (ii) and (iii) are made by an assessor that is a medical professional and/or a computer program including image processing capabilities.

Statement 51. The method of statement 50, wherein the assessor is a medical professional selected from the group consisting of general practitioner, dermatologist, oncologist, radiologist or nurse.

Statement 52. A method of assessing the severity of clinical or pre-clinical skin damage in at least one skin field in a subject comprising assessing the severity of the skin damage in the skin field and allocating that skin field into 1 of five categories of increasing skin severity based on the severity of the skin and assigning a global score to the skin field based on the categorization.

Statement 53. The method of statement 52, wherein the five categories are unaffected, mild skin field damage, moderate skin field damage, severe skin field damage, and very severe skin field damage.

Statement 54. The method of statement 53, wherein the global score assigned is
0 for unaffected;
1 for mild skin field damage;
2 for moderate skin field damage;
3 for severe skin field damage; and
4 for very severe skin field damage.

Statement 55. A method of assessing the severity of clinical or pre-clinical skin damage in at least one skin field in a subject comprising
(i) assessing the skin field as having:
a) no keratosis evident;
b) a small area of affected with few or thin keratoses;
c) patchy involvement in the zone, moderately thick keratosis, or patchy involvement in the zone with moderately thick keratoses;
d) extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratosis.

Statement 56. A method of assessing the severity of clinical or pre-clinical skin damage in at least one skin field in a subject comprising
(i) assessing the skin field as having:
a) no keratosis evident;
b) a small area of affected with few or thin keratoses;
c) patchy involvement in the zone, moderately thick keratosis, or patchy involvement in the zone with moderately thick keratoses;
d) extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratoses; and
(ii) assigning the skin field a global score based on the results of assessment (i).

Statement 57. A method of assessing the severity of clinical or pre-clinical skin damage in at least one skin field in a subject comprising
(i) selecting an assessor trained to assess the skin field as having:
a) no keratosis evident;
b) a small area of affected with few or thin keratoses;
c) patchy involvement in the zone, moderately thick keratosis, or patchy involvement in the zone with moderately thick keratoses;
d) extensive involvement of the zone with numerous thicker keratoses; extensive involvement of the zone with (A) numerous thicker keratosis with cutaneous horn; and/or (B) confluent (ie continuous) keratoses; or
e) near complete involvement of the zone with numerous thicker keratoses; and
(ii) the assessor assessing the one or more skin field in accordance with their training.

Statement 58. A method of assessing the severity of clinical or pre-clinical skin damage in at least one skin field in a subject comprising
(i) selecting an assessor trained to assess the skin field as having:
a) no keratosis evident;
b) a small area of affected with few or thin keratoses;
c) patchy involvement in the zone, moderately thick keratosis, or patchy involvement in the zone with moderately thick keratoses;
d) extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratoses; and
(ii) the assessor assessing the one or more skin field in accordance with their training, and
(iii) assigning the skin field a global score based on the results of assessment (i).

Statement 59. A non-invasive method for collecting data useful for determining severity of clinical or preclinical skin damage in at least one skin field in a subject, the method comprising:
(i) assessing the skin field as having:
a) no keratosis evident;
b) a small area of affected with few or thin keratoses;

c) patchy involvement in the zone, moderately thick keratosis, or patchy involvement in the zone with moderately thick keratoses;
d) extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratosis.

Statement 60. The method of statement 59, further comprising (ii) assigning the skin field a global score based on the results of assessment (i).

Statement 61. A method for monitoring the response of a subject to treatment for clinical or pre-clinical skin damage, the method comprising
(i) prior to the subject receiving treatment assessing the skin field as having:
b) a small area of affected with few or thin keratoses;
c) patchy involvement in the zone, moderately thick keratosis, or patchy involvement in the zone with moderately thick keratoses;
d) extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratoses; and
ii) after the subject receiving treatment assessing the skin field as having:
a) no keratosis evident;
b) a small area of affected with few or thin keratoses;
c) patchy involvement in the zone, moderately thick keratosis, or patchy involvement in the zone with moderately thick keratoses;
d) extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratosis;
and comparing the assessment of i) and ii) to monitor the subject's response to the treatment.

Statement 62. A method for monitoring the response of a subject to treatment for clinical or pre-clinical skin damage, the method comprising
(i) assessing the skin field as having:
b) a small area of affected with few or thin keratoses;
c) patchy involvement in the zone, moderately thick keratosis, or patchy involvement in the zone with moderately thick keratoses;
d) extensive involvement of the zone with numerous thicker keratoses; or
e) extensive involvement of the zone with (A) numerous thicker keratosis with cutaneous horn; and/or (B) confluent (ie continuous) keratoses, or
f) near complete involvement of the zone with numerous thicker keratoses; and
(ii) treating the skin field based on the assessment of the skin field, and
(iii) following treatment repeating the assessments in (i) and comparing the initial and repeated assessments to monitor the subject's response to the treatment.

Statement 63. The method of any one of statements 52 to 62, wherein the assessment is performed on one or more image of the skin field.

Statement 64. The method of statement 63, wherein the one or more images of the skin field are obtained prior to the assessment.

Statement 65. The method of statement 57 or 58, wherein the assessor is a trained medical professional or a computer program including image processing capabilities.

Statement 66. The method of any one of statements 55 to 65, wherein the global score assigned is 0 for (a), 1 for (b), 2 for (c), 3 for (d) and 4 for (e) or (f) respectively.

Statement 67. The method of any one of statements 52 to 54 and 66, wherein following assigning the global score the subject is treated by at least one of (a) freezing one or more lesions, (b) shaving, curetting or surgically removing one or more lesions, (c) applying a topical treatment for actinic keratosis, basal cell carcinoma or squamous cell carcinoma, and (d) radiation therapy.

Statement 68. The method of any one of statements 52 to 54 and 66 to 67, wherein the subject is assigned a global score of 3 or 4 and is treated with a skin field therapy.

Statement 69. The method of any one of statements 52 to 54 and 66 to 68, wherein the subject is assigned a global score of 4 and is treated with field radiation therapy.

Statement 70. The method of any one of statements 52 to 54 and 66 to 68, wherein the subject is assigned a global score of 3 and is treated with either field radiation therapy or the field application of a topical treatment.

Statement 71. The method of any one of statements 52 to 54 and 66 to 67, wherein the subject is assigned a global score of 2 and is treated with either the field application of a topical treatment or a lesional therapy.

Statement 72. The method of any one of statements 52 to 54 and 66 to 67, wherein the subject is assigned a global score of 1 and is treated with a lesional therapy.

Statement 73. The method of any one of statements 52 to 54 and 66 to 67, wherein
(i) when the subject is assigned a global score of 4, the subject is treated with field radiotherapy;
(ii) when the subject is assigned a global score of 3, the subject is treated with field radiotherapy or the field application of a topical treatment;
(iii) when the subject is assigned a global score of 2, the subject is treated with the field application of a topical treatment or lesional therapy; and
(iv) when the subject is assigned a global score of 1, the subject is treated with lesional therapy.

Statement 74. The method of any one of statements 1 to 73, wherein the skin field is further assessed for the presence of cancer in the skin field and/or a histologically proven history of cancer in the skin field within the past 6 months.

Statement 75. The method of any one of statements 1 to 74, wherein the method does not involve the assessment of erythema in the skin field.

Statement 76. The method of any one of statements 1 to 75, wherein the skin field is treated following its assessment and the treatment of the clinical or preclinical skin damage in the skin field prevents the development of skin cancer or further skin cancers.

Statement 77. The method of any one of statements 1 to 76, wherein the skin field is treated following its assessment and the treatment reduces the clinical and/or pre-clinical skin damage in the skin field.

Statement 78. The method of any one of statements 1 to 77, wherein the skin field is treated following its assessment and the efficacy of the treatment evaluated about 2 weeks to 2 months after treatment is ceased.

Statement 79. The method of statement 78, wherein the assessment of treatment efficacy is evaluated at least 2 weeks, 4 weeks or 6 weeks after treatment is ceased.

Statement 80. The method of statement 78 or statement 79, treatment improved the clinical and/or subclinical skin damage and optionally the improvement is maintained for 3, 6, 9, 12, 18 or 24 months.

Statement 81. The method of any one of statements 1 to 80, wherein the at least one skin field is an anatomical region of skin.

Statement 82. The method of statement 81, wherein the at least one skin field is selected from the group consisting of head, scalp (optionally divided into the occipital, right and left temporal and vertex of the scalp), tonsure of the scalp, forehead, nose (optionally the right and left halves), right cheek (optionally divided into the lower and upper right cheek), left cheek (optionally divided into the lower and upper left cheek), right ear (optionally anterior and posterior right ear), left ear (anterior and posterior left ear), neck (optionally divided into the back of the neck and front of the neck), chin, right forearm, left forearm, dorsum of the right hand, dorsum of the left hand, palm of the left hand, palm of the right hand, right lower leg, left lower leg, right upper leg, left upper leg, dorsum of the right foot, dorsum of the left foot, sole of the right foot, sole of the left foot, back (optionally the upper and lower back are separate fields), shoulders (optionally the right shoulder, left shoulder or across the top of the upper back), chest (optionally the upper chest and lower chest are considered separate fields), chest from the waist up, back from the waist up, abdomen, buttocks (optionally the right buttock and left buttock are separate fields), right upper arm, left upper arm, décolletage, or combinations thereof including the lower and upper left and/or right arm, the lower and upper left and/or right leg, the right cheek and right ear, the left cheek and left ear, the right cheek and right half of the forehead and optionally also the right ear and/or right half of the nose, the right half of the face, left cheek and left half of the forehead and optionally also the left ear and/or left half of the nose, the left half of the face, the chin and lower left and right cheeks (ie the lower third of the face), the nose and upper right and left cheeks (ie the middle third of the face), and the nose, upper right and left cheeks, and right and left ears.

Statement 83. The method of statement 81, wherein the at least one skin field is selected from the group consisting of head, scalp, occipital scalp, right temporal scalp, left temporal scalp, vertex of the scalp, tonsure of the scalp, forehead, nose, right cheek, left cheek, right ear, anterior right ear, posterior right ear, anterior left ear, posterior left ear, left ear, neck, back of the neck, front of the neck, right forearm, left forearm, dorsum of the right hand, dorsum of the left hand, right lower leg, left lower leg, right upper leg, left upper leg, dorsum of the right foot, dorsum of the left foot, right shoulder, left shoulder, upper back, lower back, central upper back, right shoulder, left shoulder, upper chest, lower chest, right upper arm, left upper arm, décolletage, or combinations thereof including combinations of portions thereof, such as the lower and upper left and/or right arm, the lower and upper left and/or right leg, the right cheek and right ear, the left cheek and left ear, the right cheek and right half of the forehead and optionally also the right ear and/or right half of the nose, the right half of the face, left cheek and left half of the forehead and optionally also the left ear and/or left half of the nose, and the left half of the face.

Statement 84. The method of statement 81, wherein the at least one skin field is selected from the group consisting of scalp, tonsure of the scalp, forehead, nose, right cheek, left cheek, right ear, left ear, front of the neck, back of the neck, right forearm, left forearm, dorsum of the right hand, dorsum of the left hand, dorsum of the right foot, dorsum of the left foot, right lower leg, left lower leg, right shoulder, left shoulder, upper chest, and upper back.

Statement 85. The method of any one of statements 1-84, wherein the skin field is a minimum of 25 $cm^2$ in area.

Statement 86. The method of any one of statements 1-85, wherein the skin field is a maximum of 1,000 $cm^2$ in area.

Statement 87. The method of any one of statements 1-88, wherein the clinical or pre-clinical skin damage is clinical skin damage.

Statement 88. The method of any one of statements 1-89, wherein the clinical or pre-clinical skin damage is pre-cancerous skin damage, cancerous skin damage or a combination thereof.

Statement 89. The method of statement 88, wherein the cancerous skin damage is non-melanoma skin cancer.

Statement 90. The method of any one of statements 1-88, wherein the clinical skin damage is actinic keratosis, Bowenoid keratosis, Bowen's disease, skin field cancerization and/or non-melanoma skin cancer such as SCC, BCC and/or MCC.

Statement 91. A method for treating clinical or pre-clinical skin damage in a skin field of a subject, wherein the skin field has been allocated a skin cancerization field index (SCFI) score of at least 1 as determined by a process comprising the steps of:
(a) selecting and assessing at least one skin field for
    (i) the number of keratoses in the skin field;
    (ii) the thickness of the thickest keratosis in the skin field; and
    (iii) the proportion of the field affected by clinical or subclinical skin damage;
(b) assigning a score of 0 to 3 for assessment (i), a score of 0 to 3 for assessment (ii), and a score of 0 to 5 for assessment (iii); and
(c) adding the score for assessment (i) to the score for assessment (ii) and then multiplying the sum of those scores by the score for assessment (iii) to obtain the SCFI score;
the method for treating comprising:
A. treating the skin field with a field therapy when the SCFI score is 10 or greater; or
B. treating the skin field with a lesional therapy when the SCFI score is 1 to 9.

Statement 92. The method of statement 91, wherein a score of 1-3 is allocated for the skin field in assessment (i) as follows:
1 for 5 or fewer discrete lesions in the skin field and no continuous keratoses;
2 for 6 to 15 discrete lesions in the skin field and no continuous keratosis; and
3 for continuous keratosis and/or more than 15 discrete lesions in the skin field.

Statement 93. The method of statement 91 or 92, wherein a score of 0-3 is allocated for the skin field in assessment (ii) as follows:
0 for no thickness;
1 for about 1 mm thick;
2 for greater than 1 mm to about 3 mm thick; and
3 for greater than 3 mm thick.

Statement 94. The method of statement 91 or 92, wherein a score of 0-3 is allocated for the skin field in assessment (ii) in accordance with the Olsen score.

Statement 95. The method of statement 91 or 92, wherein a score of 0-3 is allocated for the skin field in assessment (ii) as follows:
0 for no thickness;
1 for just perceptible thickness;
2 for easily felt or seen thickness; and
3 for cutaneous horns.

Statement 96. The method of statement 91-95, wherein a score of 0-5 is allocated for the skin field in assessment (iii) as follows
0 for no area affected;
1 for 1-5% of the area affected;
2 for less than ⅓ of the area affected;
3 for ⅓-⅔ of the area affected;
4 for greater than ⅔ of the area to 95% of the area affected, or
5 for 96-100% of the area in the skin field affected.

Statement 97. The method of statement 91-95, wherein a score of 0-5 is allocated for the skin field in assessment (iii) as follows
0 for no area affected;
1 for 1-5% of the area affected;
2 for 6-33% of the area affected;
3 for 34-66% of the area affected;
4 for 67-95% of the area affected, or
5 for 96-100% of the area in the skin field affected.

Statement 98. The method of statement 91-97, wherein the field therapy is radiation therapy, the field application of a topical treatment, or a topical treatment followed by radiation therapy.

Statement 99. The method of statement 91-98, wherein the skin field has an SCFI of 10 to 19 and is treated with the field application of a topical treatment.

Statement 100. The method of statement 91-98, wherein the skin field has an SCFI of 20 to 30 and is treated with either field radiation therapy or the field application of a topical treatment.

Statement 101. The method of statement 91-98, wherein the skin field has an SCFI of 20 to 25 and is treated with either field radiation therapy or the field application of a topical treatment.

Statement 102. The method of statement 91-98, wherein the skin field has an SCFI of 26 to 30 and is treated with field radiation therapy.

Statement 103. The method of statement 91-98, wherein the skin field has an SCFI of 24 or 25 and a score of 3 in assessment (ii) and is treated with field radiation therapy.

Statement 104. The method of statement 91-97, wherein the lesional therapy is chosen from (a) freezing one or more lesions with liquid nitrogen; (b) shaving, curetting or surgically removing one or more lesions; and (c) applying a topical treatment to one or more lesions.

Statement 105. The method of statement 91-97, wherein the topical treatment is chosen from 5-fluorouracil, imiquimod, ingenol mebutate, diclofenac, and photodynamic therapy.

Statement 106. The method of statement 91-105, wherein the clinical skin damage is chosen from actinic keratosis, Bowenoid keratosis, Bowen's disease, skin field cancerization, and non-melanoma skin cancer.

Statement 107. The method of statement 106, wherein the non-melanoma skin cancer is chosen from squamous cell carcinoma, basal cell carcinoma, and Merkel cell carcinoma.

Statement 108. The method of statement 91-107, wherein the at least one skin field is chosen from head, scalp, occipital scalp, right temporal scalp, left temporal scalp, vertex of the scalp, tonsure of the scalp, forehead, nose, left half of nose, right half of nose, right cheek, upper right cheek, lower right cheek, left cheek, upper left cheek, lower left cheek, right ear, anterior right ear, posterior right ear, left ear, anterior left ear, posterior left ear, entire neck, back of the neck, front of the neck, chin, right forearm, left forearm, dorsum of the right hand, dorsum of the left hand, palm of the left hand, palm of the right hand, right lower leg, left lower leg, right upper leg, left upper leg, dorsum of the right foot, dorsum of the left foot, sole of the right foot, sole of the left foot, whole back, upper back, lower back, both shoulders, right shoulder left shoulder, across the top of the upper back, chest, upper chest, lower chest, chest from the waist up, back from the waist up, abdomen, buttocks, left buttock, right buttock, right upper arm, left upper arm, and décolletage, or combinations thereof.

Statement 109. The method of statement 91-107, wherein the at least one skin field is chosen from scalp, tonsure of the scalp, forehead, nose, right cheek, left cheek, right ear, left ear, front of the neck, back of the neck, right forearm, left forearm, dorsum of the right hand, dorsum of the left hand, dorsum of the right foot, dorsum of the left foot, right lower leg, left lower leg, right shoulder, left shoulder, upper chest, and upper back.

Statement 110. A method for treating clinical or pre-clinical skin damage in a skin field of a subject with a skin cancerization field index (SCFI) score of at least 1, the method comprising the steps of:
determining a skin cancerization field index (SCFI) score by
(a) selecting and assessing at least one skin field for
(i) the number of keratoses in the skin field;
(ii) the thickness of the thickest keratosis in the skin field; and
(iii) the proportion of the field affected by clinical or subclinical skin damage; and
(b) assigning a score of 0 to 3 for assessment (i), a score of 0 to 3 for assessment (ii), and a score of 0 to 5 for assessment (iii);
(c) adding the score for assessment (i) to the score for assessment (ii) and then multiplying the sum of those scores by the score for assessment (iii) to obtain the SCFI score; and
treating the clinical or pre-clinical skin damage, wherein
if the SCFI score is 10 or greater, then the skin damage is treated with a field therapy; and
if the SCFI score is 1 to 9, then the skin damage is treated with a lesional therapy.

The invention claimed is:
1. A method for treating clinical or pre-clinical skin damage in a skin field of a subject, wherein the skin field has been allocated a global score of at least 1 by a process comprising the steps of:
(i) assessing the skin field for:
(a) a small area affected with few or thin keratoses;
(b) patchy involvement in the zone, moderately thick keratosis, or patchy involvement in the zone with moderately thick keratoses;
(c) extensive involvement of the zone, numerous thicker keratosis, or extensive involvement of the zone with numerous thicker keratoses;
(d) extensive involvement of the zone with (A) numerous thicker keratosis with cutaneous horn; and/or (B) confluent (i.e. continuous) keratoses, or

(e) near complete involvement of the zone with numerous thicker keratosis, wherein the assessment does not involve assessment of erythema in the skin field; and (ii) assigning the skin field a global score based on the results of assessment (i) wherein the global score assigned is 1 for (a), 2 for (b), 3 for (c) and 4 for (d) or (e);

the method for treating the clinical or pre-clinical skin damage comprising:

treating the skin field with field radiotherapy when the skin field is assigned a global score of 4;

treating the skin field with field radiotherapy and/or applying a topical treatment when the skin field is assigned a global score of 3;

A. treating the skin field by applying a topical treatment and/or lesional therapy when the skin field is assigned a global score of 2; and B. treating the skin field with lesional therapy when the skin field is assigned a global score of 1.

2. The method of claim 1, wherein the skin field is further assessed for the presence of cancer and/or a histologically proven history of cancer in the skin field within the past 6 months.

3. The method of claim 1, wherein the treatment of the clinical or preclinical skin damage in the skin field prevents the development of skin cancer or further skin cancers.

4. The method of claim 1, wherein the at least one skin field is an anatomical region of skin.

5. The method of claim 4, wherein the at least one skin field is selected from the group consisting of head, scalp, occipital scalp, right temporal scalp, left temporal scalp, vertex of the scalp, tonsure of the scalp, forehead, nose, left half of nose, right half of nose, right cheek, lower right cheek, upper right cheek, left cheek, upper left cheek, lower left cheek, right ear, anterior right ear, posterior right ear, left ear, anterior left ear, posterior left ear, entire neck, back of the neck, front of the neck, chin, right forearm, left forearm, dorsum of the right hand, dorsum of the left hand, palm of the left hand, palm of the right hand, right lower leg, left lower leg, right upper leg, left upper leg, dorsum of the right foot, dorsum of the left foot, sole of the right foot, sole of the left foot, whole back, upper back, lower back, both shoulders, right shoulder, left shoulder, across the top of the upper back, chest, upper chest, lower chest, chest from the waist up, back from the waist up, abdomen, buttocks, left buttock, right buttock, right upper arm, left upper arm, and décolletage, or combinations thereof.

6. The method of claim 4, wherein the at least one skin field is selected from the group consisting of head, scalp, occipital scalp, right temporal scalp, left temporal scalp, vertex of the scalp, tonsure of the scalp, forehead, nose, right cheek, left cheek, right ear, anterior right ear, posterior right ear, anterior left ear, posterior left ear, left ear, entire neck, back of the neck, front of the neck, right forearm, left forearm, dorsum of the right hand, dorsum of the left hand, right lower leg, left lower leg, right upper leg, left upper leg, dorsum of the right foot, dorsum of the left foot, right shoulder, left shoulder, upper back, lower back, right shoulder, left shoulder, upper chest, lower chest, right upper arm, left upper arm, décolletage, or combinations thereof.

7. The method of claim 4, wherein the at least one skin field is selected from the group consisting of scalp, tonsure of the scalp, forehead, nose, right cheek, left cheek, right ear, left ear, front of the neck, back of the neck, right forearm, left forearm, dorsum of the right hand, dorsum of the left hand, dorsum of the right foot, dorsum of the left foot, right lower leg, left lower leg, right shoulder, left shoulder, upper chest, and upper back.

8. The method of claim 1, wherein the skin field is a minimum of 25 cm$^2$ in area.

9. The method of claim 1, wherein the skin field is a maximum of 1,000 cm$^2$ in area.

10. The method of claim 1, wherein the clinical or pre-clinical skin damage is clinical skin damage.

11. The method of claim 1, wherein the clinical or pre-clinical skin damage is pre-cancerous skin damage, cancerous skin damage or a combination thereof.

12. The method of claim 11, wherein the cancerous skin damage is non-melanoma skin cancer.

13. The method of claim 1, wherein the clinical skin damage is actinic keratosis, Bowenoid keratosis, Bowen's disease, skin field cancerisation and/or non-melanoma skin cancer such as SCC, BCC and/or MCC.

14. The method of claim 1, wherein the assessment is performed by a medical professional.

15. The method of claim 1, wherein the assessment is performed on one or more image(s) of the skin field.

16. The method of claim 15, wherein the one or more images of the skin field are obtained prior to the assessment.

* * * * *